(12) United States Patent
Rodriguez-Araujo et al.

(10) Patent No.: US 12,312,584 B2
(45) Date of Patent: May 27, 2025

(54) cGMP EXOSOME LOADED THERAPEUTICS FOR TREATING SICKLE CELL DISEASE

(71) Applicant: Exosome Therapeutics, Inc., San Diego, CA (US)

(72) Inventors: Gerardo Rodriguez-Araujo, Rancho Santa Fe, CA (US); Stephen R. Puckett, Sr., Indian Land, SC (US); Stephen R. Puckett, Jr., Gainesville, FL (US); Mitchell W. Puckett, Matthews, NC (US)

(73) Assignee: EXOSOME THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/387,017

(22) Filed: Nov. 4, 2023

(65) Prior Publication Data
US 2024/0076669 A1 Mar. 7, 2024

Related U.S. Application Data

(63) Continuation-in-part of application No. 16/688,944, filed on Nov. 19, 2019, now abandoned, and a continuation-in-part of application No. 16/688,954, filed on Nov. 19, 2019, now abandoned, and a continuation-in-part of application No. 16/591,502, filed on Oct. 2, 2019, now abandoned, and a continuation-in-part of application No. 16/591,483, filed on Oct. 2, 2019, now abandoned, said application No. 16/688,954 is a continuation-in-part of application No. 16/591,483, filed on Oct. 2, 2019, now abandoned, which is a continuation-in-part of application No. 16/591,502, filed on Oct. 2, 2019, now abandoned, said application No. 16/688,944 is a continuation-in-part of application No. 16/591,502, filed on Oct. 2, 2019, now abandoned, and a continuation-in-part of application No. 16/591,483, filed on Oct. 2, 2019, now abandoned.

(60) Provisional application No. 62/770,640, filed on Nov. 21, 2018, provisional application No. 62/769,711, filed on Nov. 20, 2018, provisional application No. 62/769,774, filed on Nov. 20, 2018, provisional application No. 62/769,123, filed on Nov. 19, 2018, provisional application No. 62/740,396, filed on Oct. 2, 2018, provisional application No. 62/740,391, filed on Oct. 2, 2018, provisional application No. 62/740,382, filed on Oct. 2, 2018.

(51) Int. Cl.
| | |
|---|---|
| C12N 15/113 | (2010.01) |
| A61K 35/28 | (2015.01) |
| A61K 47/10 | (2017.01) |
| A61K 47/18 | (2017.01) |
| A61K 47/34 | (2017.01) |
| A61P 7/00 | (2006.01) |
| C07K 14/47 | (2006.01) |
| C12N 15/86 | (2006.01) |

(52) U.S. Cl.
CPC ............ *C12N 15/113* (2013.01); *A61K 35/28* (2013.01); *A61K 47/10* (2013.01); *A61K 47/18* (2013.01); *A61K 47/34* (2013.01); *A61P 7/00* (2018.01); *C07K 14/47* (2013.01); *C12N 15/86* (2013.01)

(58) Field of Classification Search
CPC .................. C12N 15/113; C12N 15/86; C12N 2740/10043; C12N 2750/14143; C12N 2310/14; C12N 2320/32; C12N 15/88; A61P 7/00; A61K 35/28
USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 2004/0018191 A1 | 1/2004 | Wang et al. |
| 2008/0248024 A1 | 10/2008 | Lee et al. |
| 2009/0281167 A1 | 11/2009 | Shen et al. |
| 2009/0304693 A1 | 12/2009 | Ghayur et al. |
| 2015/0232883 A1 | 8/2015 | Dahlman et al. |
| 2015/0376281 A1 | 12/2015 | Xiong et al. |
| 2018/0117117 A1 | 5/2018 | Choi et al. |
| 2018/0193270 A1 | 7/2018 | Bolen et al. |
| 2019/0060483 A1* | 2/2019 | Dooley .............. A61K 47/6917 |
| 2019/0391163 A1 | 12/2019 | Stemmer et al. |
| 2020/0101016 A1 | 4/2020 | Rodriguez-Araujo et al. |
| 2020/0102563 A1 | 4/2020 | Rodriguez-Araujo et al. |

(Continued)

FOREIGN PATENT DOCUMENTS

| | | |
|---|---|---|
| CA | 3071350 A1 | 2/2019 |
| EP | 3438250 A1 | 2/2019 |

(Continued)

OTHER PUBLICATIONS

Lu et al (Asian J. Pharmaceutical Sciences, vol. 13, pp. 1-11 (2018)) (Year: 2018).*

(Continued)

*Primary Examiner* — Jane J Zara
(74) *Attorney, Agent, or Firm* — COOLEY LLP

(57) ABSTRACT

A composition for treating sickle cell disease includes a cGMP exosome having a size range between 60 nm to 120 nm, which may be extracted from a human mesenchymal stem cell (hMSC) or human PBMC at 320,000 g, wherein the cGMP exosome may be loaded with a Hemoglobin Subunit Beta (HBB) DNA plasmid carrying a gene encoding a normal beta chain of hemoglobin and alone or in combination with a short interference RNA (siRNA) that silences the translation of the SNP rs334 (A) mutation of the beta chain of a Hemoglobin A protein.

6 Claims, 27 Drawing Sheets
Specification includes a Sequence Listing.

(56) References Cited

U.S. PATENT DOCUMENTS

| | | |
|---|---|---|
| 2020/0157541 A1 | 5/2020 | Rodriguez-Araujo et al. |
| 2020/0215114 A1 | 7/2020 | Rodriguez-Araujo et al. |
| 2020/0338158 A1 | 10/2020 | Liu |
| 2021/0177757 A1 | 6/2021 | Bolen et al. |
| 2021/0380985 A1 | 12/2021 | Hinkle et al. |
| 2022/0072158 A1 | 3/2022 | Chen et al. |

FOREIGN PATENT DOCUMENTS

| | | | |
|---|---|---|---|
| EP | 3616724 A1 | 3/2020 | |
| WO | WO-2010127195 A2 | 11/2010 | |
| WO | WO-2013126794 A1 | 8/2013 | |
| WO | WO-2015089419 A2 | 6/2015 | |
| WO | WO-2015089465 A1 | 6/2015 | |
| WO | WO-2016187717 A1 | 12/2016 | |
| WO | WO-2016205613 A1 | 12/2016 | |
| WO | WO-2017053729 A1 | 3/2017 | |
| WO | WO-2017074688 A1 * | 5/2017 | C12Q 1/683 |
| WO | WO-2017173034 A1 | 10/2017 | |
| WO | WO-2018156649 A1 | 8/2018 | |
| WO | WO-2019051237 A1 * | 3/2019 | C07K 14/195 |
| WO | WO-2019118826 A1 | 6/2019 | |
| WO | WO-2019157535 A1 | 8/2019 | |
| WO | WO-2019175428 A1 | 9/2019 | |

OTHER PUBLICATIONS

Hoshino et al (Nature, vol. 527, pp. 329-347 (2015)) (Year: 2015).*
Hoban et al (Molecular Therapy, vol. 24, No. 9, pp. 1561-1569 (2016)) (Year: 2016).*
Hong et al (Isolation of Biologically Active Exosomes from Plasma of Patients with Cancer, Methods in Molecular Biology, vol. 1633, pp. 1-18 (2017)) (Year: 2017).*
Mendt et al (JCI Insight, vol. 3, No. 8, e99263, pp. 1-22 (2018)) (Year: 2018).*
Pachler et al (Cytotherapy, vol. 19, pp. 458-472 (2017)) (Year: 2017).*
Andriolo et al (Frontiers in Physiology, vol. 9, Article 1169, pp. 1-10 (2018)) (Year: 2018).*
Arrighetti, N. et al., "Exosome-like nanovectors for drug delivery in cancer," Curr Med Chem, 26:6132-48 (2019); 10.2174/0929867325666180831150259.
Bath, L. F. et al., "Bone Turnover and Growth during and after Chemotherapy in Children with Solid Tumors," Pediatr Res, 55(2):224-230 (2004).
Beit-Yannai, E. et al., "Physical exosome: exosome interactions," J Cell Mol Med., 22(3):2001-2006 (2018); doi: 10.1111/jcmm.13479.
Biswas, M. et al., "Gene Therapy with Regulatory T Cells: a Beneficial Alliance," Front Immunol., 9:554 (2018), 13 pages; doi: 10.3389/fimmu.2018.00554.
Bunggulawa, E. J. et al., "Recent advancements in the use of exosomes as drug delivery systems," J Nanobiotechnology, 16(1):81 (2018), 13 pages; doi: 10.1186/s12951-018-0403-9.
Chiriacò, M. S. et al., "Lab-on-Chip for Exosomes and Microvesicles Detection and Characterization," Sensors (Basel), 18(10):3175 (2018), 41 pages; doi: 10.3390/s18103175.
Colella, P. et al., "Emerging Issues in AAV-Mediated In Vivo Gene Therapy," Mol Ther Methods Clin Dev., 8:87-104 (2018); doi: 10.1016/j.omtm.2017.11.007.
Dykxhoorn, D. M. et al., "Determinants of specific RNA interference-mediated silencing of human ß-globin alleles differing by a single nucleotide polymorphism," Proc Natl Acad Sci USA, 103(15):5953-8 (2016); doi: 10.1073/pnas.0601309103. Epub Apr. 3, 2006.
Ferla, R. et al., "Non-clinical Safety and Efficacy of an AAV2/8 Vector Administered Intravenously for Treatment of Mucopolysaccharidosis Type VI," Mol Ther Methods Clin., 6:143-158 (2017).
Gimona, M. et al., "Manufacturing of human extracellular vesicle-based therapeutics for clinical use," Int J Mol Sci., 18:1190 (2017), 19 pages; doi: 10.3390/ijms18061190.
Grievink, H. W. et al., "Comparison of Three Isolation Techniques for Human Peripheral Blood Mononuclear Cells: Cell Recovery and Viability, Population Composition, and Cell Functionality," 14(5):410-415 (2016).
International Search Report and Written Opinion mailed Dec. 18, 2019 for International Application No. PCT/US2019/054363, 8 pages.
International Search Report and Written Opinion mailed Dec. 26, 2019 for International Application No. PCT/US2019/054364, 8 pages.
International Search Report and Written Opinion mailed Mar. 10, 2020 for International Application No. PCT/US2019/062293, 9 pages.
International Search Report and Written Opinion mailed Mar. 5, 2020 for International Application No. PCT/US2019/062291, 10 pages.
Iyer, N. S. et al., "Chemotherapy-only treatment effects on long-term neurocognitive functioning in childhood ALL survivors: a review and meta-analysis," Blood, 126:346-353 (2015).
Janas, T. et al., "Mechanisms of RNA loading into exosomes," FEBS Lett., 589(13):1391-8 (2015); doi: 10.1016/j.febslet.2015.04.036. Epub Apr. 30, 2015.
Jin, Y. et al., "MiR-214 regulates the pathogenesis of patients with coronary artery disease by targeting VEGF," Mol Cell Biochem., 402(1-2):111-22 (2015); doi: 10.1007/s11010-014-2319-5. Epub Jan. 10, 2015.
Khan, M. S. & Roberts, M. S., "Challenges and innovations of drug delivery in older age," Adv Drug Delivery Rev., 135:3-38 (2018); doi: 10.1016/j.addr.2018.09.003.
Kim, S. M. et al., "Cancer-derived exosomes as a delivery platform of CRISPR/Cas9 confer cancer cell tropism-dependent targeting," J. Controlled Release, 266: 8-16 (2017).
Kosaka, N. et al., "Neutral sphingomyelinase 2 (nSMase2)-dependent exosomal transfer of angiogenic microRNAs regulate cancer cell metastasis," J Biol Chem., 288(15):10849-59 (2013); doi: 10.1074/jbc.M112.446831. Epub Feb. 25, 2013.
Kuate, S. et al., "Exosomal vaccines containing the S protein of the SARS coronavirus induce high levels of neutralizing antibodies," Virology, 362(1):26-37 (2007); doi: 10.1016/j.virol.2006.12.011. Epub Jan. 26, 2007.
Marcus, M. E. & Leonard, J. N., "FedExosomes: Engineering Therapeutic Biological Nanoparticles that Truly Deliver," Pharmaceuticals (Basel), 6(5):659-680 (2013); doi: 10.3390/ph6050659.
Mathiyalagan, P. et al., "Angiogenic Mechanisms of Human CD34+ Stem Cell Exosomes in the Repair of Ischemic Hindlimb," Circ Res, 120(9):1466-1476 (2017); doi: 10.1161/CIRCRESAHA.116.310557. Epub Mar. 15, 2017.
Miliotou, A. N. & Papadopoulou, L. C., "CAR T-Cell Therapy: A New Era in Cancer Immunotherapy," Curr Pharm Biotechnol., 19(1):5-18 (2018); doi: 10.2174/1389201019666180418095526.
Mingozzi, F., "AAV Immunogenicity: A Matter of Sensitivity," Mol Ther., 26(10):2335-2336 (2018); doi: 10.1016/j.ymthe.2018.09.001.
[No Author Listed] Center for Disease Control, "What is Sickle Cell Disease," Website page, 1 page; //https://www.cdc.gov/sickle-cell/?CDC_AAref_Val=https://www.cdc.gov/ncbddd/sicklecell/facts//.
Pepper, J. W. et al., "Cancer research meets evolutionary biology," Evol Appl., 2(1):62-70 (2009); doi: 10.1111/j.1752-4571.2008.00063.x.
Ray, K. K. et al., "Inclisiran in Patients at High Cardiovascular Risk with Elevated LDL Cholesterol," N Engl J Med., 376(15):1430-1440 (2017); doi: 10.1056/NEJMoa1615758. Epub Mar. 17, 2017.
Sheldon, H. et al., "New mechanism for Notch signaling to endothelium at a distance by Delta-like 4 incorporation into exosomes," Blood, 116(13):2385-94 (2010); doi: 10.1182/blood-2009-08-239228. Epub Jun. 17, 2010.
Smith, T. T. et al., "In situ programming of leukaemia-specific T cells using synthetic DNA nanocarriers", Nature Nanotechnology, 12(8): 813-820 (2017).
Wei, C. et al., "Exosomal miR-1246 in body fluids is a potential biomarker for gastrointestinal cancer," Biomarkers in Medicine, 12(10):1185-1196 (2018); https://doi.org/10.2217/bmm-2017-0440.

(56) References Cited

OTHER PUBLICATIONS

Wikipedia, "Sodium-glucose transport proteins," printed Feb. 7, 2022, 6 pages.

\* cited by examiner

Figure 5

| | Autologous | | | | Allogenic | |
|---|---|---|---|---|---|---|
| | Min | Max | Optimal Min | Optimal Max | Optimal Min | Optimal Max |
| Size (nM) | 30 | 130 | 55 | 120 | 30 | 130 |
| Expansion (nM) | 60 | 260 | 110 | 200 | 60 | 260 |
| Electrical Charge | negative | negative | negative | negative | negative | negative |
| Membrane Affinity | high | high | high | high | high | high |
| Biodistribution | high | moderate | high | moderate | high | moderate |
| Potency | high | moderate | high | moderate | high | moderate |
| Stability | moderate | high | moderate | high | moderate | high |
| Therapeutic Cargo | RNA, DNA, editing tools, nucleases | DNA, proteins, megalonucleases | RNA, DNA, editing tools, nucleases | DNA, proteins, megalonucleases | RNA, DNA, editing tools, nucleases | DNA, proteins, megalonucleases |
| Immunogenicity | none | none | none | none | potential ADA, NAbs | potential ADA, NAbs |
| Loading Efficiency | >95% | >95% | >95% | >95% | >95% | >95% |
| Purity | >98% | >98% | >98% | >98% | >98% | >98% |
| Couple | <5% | <3% | <5% | <3% | <5% | <3% |
| Therapeutic Unit Comp#1 | pDNA (2-4 plasmids/exosome/pcell) >95% loaded at this concent | | | | | |
| Therapeutic Unit Comp#2 | siRNA (2pg+1siRNA/exosome/pcell) + pDNA (2-4 plasmids/exosome/pcell) >95% loaded at this concent | | | | | |
| Therapeutic Unit Comp#3 | Nuclease (34 Kda/exosome/pcell) >95% loaded at this concent | | | | | |

QA QC: Chromatography, MS, quantitative assays, 2nd, 3rd line of QA/QC

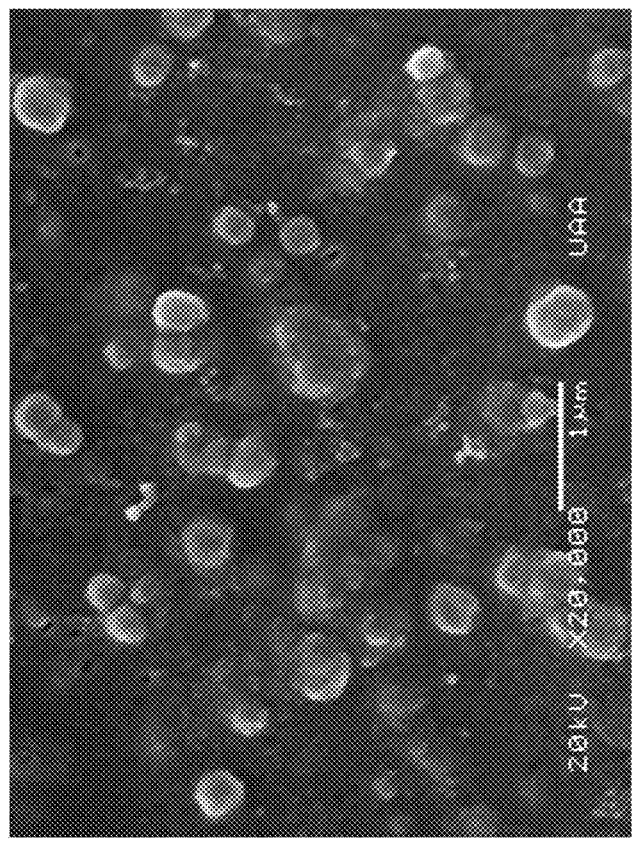
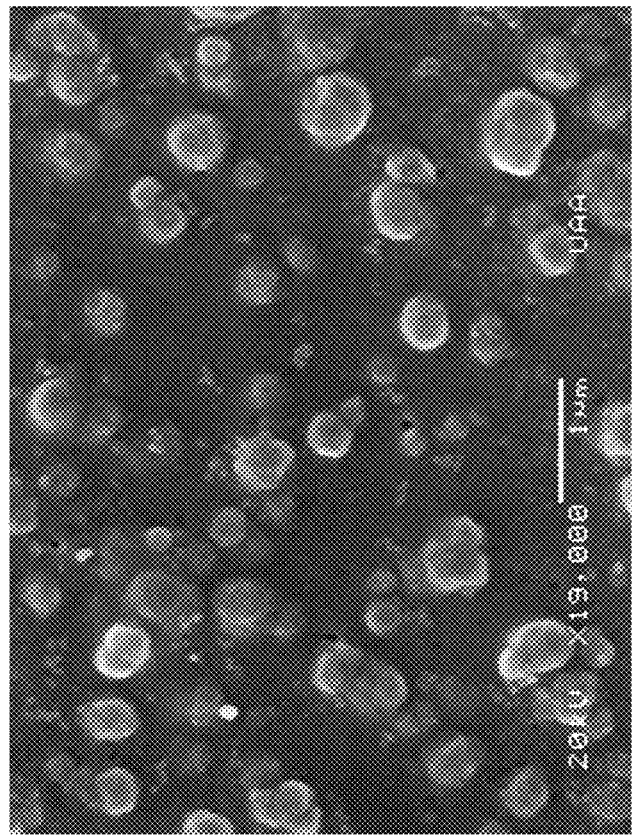
FIGURE 22A

FIGURE 22B
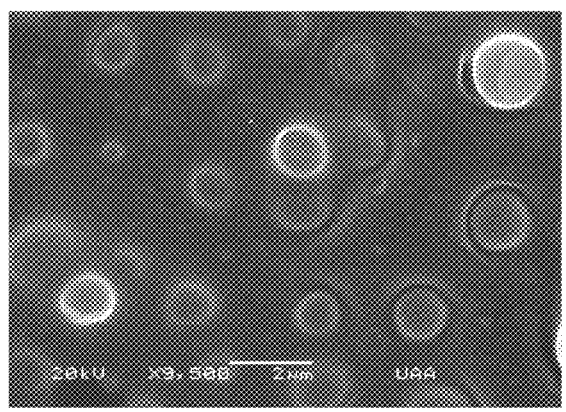
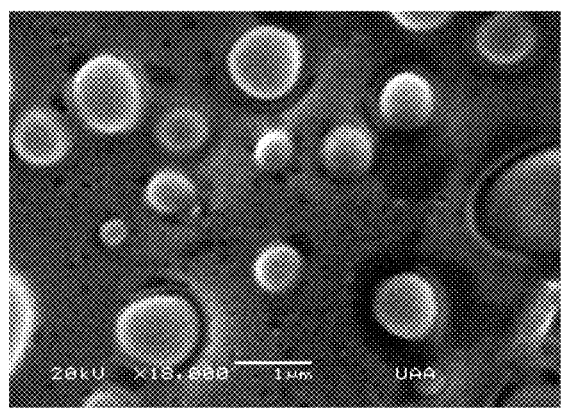
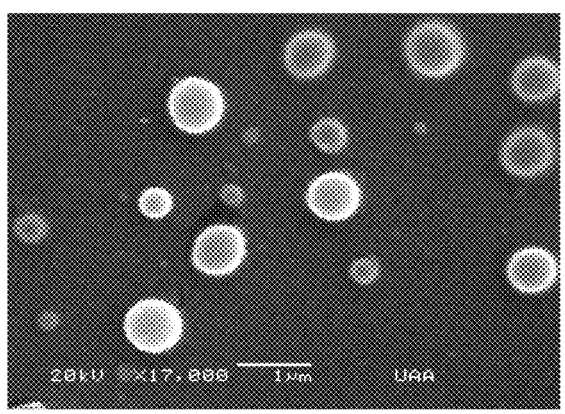
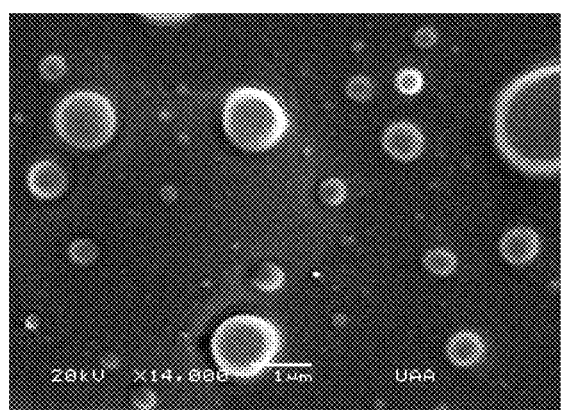
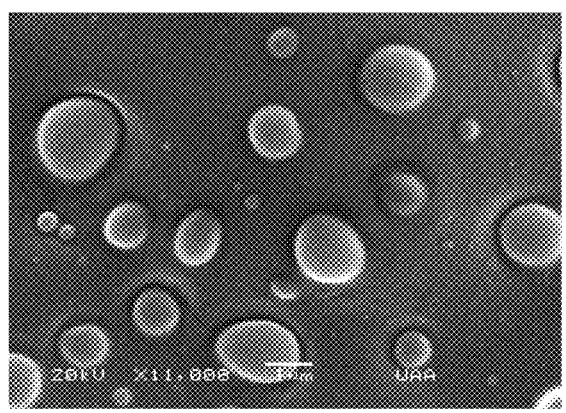
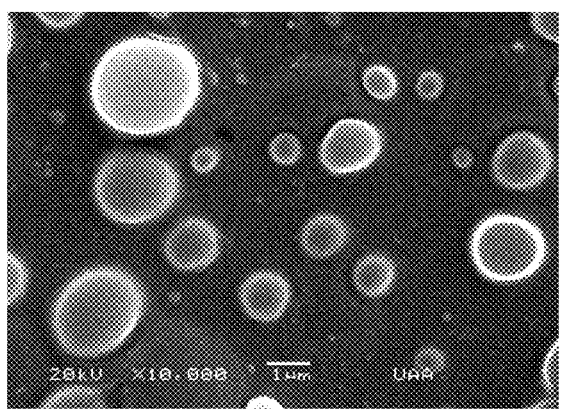

SEQUENCE LISTING

```
Sequence total quantity: 8
SEQ ID NO: 1             moltype = DNA  length = 1080
FEATURE                  Location/Qualifiers
source                   1..1080
                         mol_type = other DNA
                         note = Human DNA Plasmid
                         organism = synthetic construct
                         plasmid = SEQ ID GR1 (1) beta hemoglobin with GFP: DNA and
                           amino acid. Amino Acid:    AATMVHLTPEEKSAVTALWGKVNVDEVGGEALGR
                           LLVVYPWTQRFFESFGDLSTPD
                         AVMGNPKVKAHGKKVLGAFSDGLAHLDNLKGTFATLSELHCDKLHVDPENFRLLGNVLV
                         CVLAHHFGKEFTPPVQAAYQKVVAGVANALAHKYHGGGSGSMVSKGEELFTGVVPILVE
                         LDGDVNGHKFSVSGEGEGDATYGKLTLKFICTTGKLPVPWPTLVTTFTYGVQCFARYPD
                         HMKQHDFFKSAMPEGYVQERTIFFKDDGNYKTRAEVKFEGDTLVNRIELKGIDFKEDGN
                         ILGHKLEYNYNSHKVYITADKQKNGIKVNFKTRHNIEDGSVQLADHYQQNTPIGDGPVL
                         LPDNHYLSTQSALSKDPNEKRDHMVLLEFVTAAGITLGMDELYK
SEQUENCE: 1
ggtaccgccg ccaccatggt gcacctgaca cctgaagaga agtccgccgt gacagccctg   60
tggggcaaag tgaatgtgga tgaagttggc ggcgaggccc tgggtagact gctggttgtt  120
tacccctgga cacagcggtt cttcgagagc ttcggcgatc tgagcacacc cgatgccgtg  180
atgggcaacc ctaaagtgaa ggcccacggc aagaaagtgc tgggcgcctt ttctgatgga  240
ctgccccacc tggacaatct gaagggcacc tttgccacac tgagcgagct gcactgcgac  300
aagctgcacg tggaccccga gaactttagg ctgctgggca atgtgctcgt gtgcgtgctg  360
gcccatcact tcggcaaaga attcacccct cctgtgcagg ccgcctacca gaaagttgtt  420
gccggcgtgg caaatgccct ggctcacaag tatcatggcg gcggatctgg cagcatggtg  480
tccaaaggcg aggaactgtt taccggcgtg gtgcccattc tggtggaact ggacggggat  540
gtgaacggcc acaagtttag cgttagcggc gaaggcgaag gggatgccac atacggaaag  600
ctgaccctga agttcatctg caccaccggc aagctgcctg tgccttggcc tacactggtc  660
accacctta cctacggcgt gcagtgcttc gccagatatc ccgaccatat gaagcagcac  720
gacttcttca agagcgccat gcctgagggc tacgtgcaag agcggaccat cttctttaag  780
gacgacggca actacaagac ccgggctgaa gtgaagttcg agggcgacac cctggtcaac  840
cggatcgagc tgaagggaat cgacttcaaa gaggacggca acatcctggg ccacaagctc  900
gagtacaact acaacagcca caaggtgtac atcaccgccg acaagcagaa aaacggcatc  960
```

```
aaagtgaact tcaagacgcg gcacaacatc gaggacggct ctgtgcagct ggccgaccac  1020
tatcagcaga acacacccat cggagatggc cccgttctgc tgcccgataa ccactacctg  1080

SEQ ID NO: 2           moltype = DNA   length = 462
FEATURE                Location/Qualifiers
source                 1..462
                       mol_type = other DNA
                       note = Human DNA Plasmid
                       organism = synthetic construct
                       plasmid = SEQ ID GR1 (2) beta hemoglobin without GFP: DNA
                         and amino acid. Amino acid:
                         AATMVHLTPEEKSAVTALWGKVNVDEVGGEALGRLLVVYPWTQRFFESFGDLSTPD
                         AVMGNPKVKAHGKKVLGAFSDGLAHLDNLKGTFATLSELHCDKLHVDPENFRLLGNVLV
                         CVLAHHFGKEFTPPVQAAYQKVVAGVANALAHKYH
SEQUENCE: 2
gcggcgacca tggtgcatct gacccggaa gaaaaagcg cggtgaccgc gctgtgggc     60
aaagtgaacg tggatgaagt gggcggcgaa gcgctgggcc gctgctggt ggtgtatccg  120
tggacccagc gcttttttga aagctttggc gatctgagca cccgatgc ggtgatgggc   180
aacccgaaag tgaaagcgca tggcaaaaaa gtgctgggcg cgtttagcga tggcctggcg  240
catctggata acctgaaagg caccttttgcg accctgagcg aactgcattg cgataaactg  300
catgtggatc cggaaaactt tcgcctgctg ggcaacgtgc tggtgtgcgt gctggcgcat  360
cattttggca aagaatttac cccgccggtg caggcggcgt atcagaaagt ggtggcgggc  420
gtggcgaacg cgctggcgca taaatatcat tacctgtaat ag                    462

SEQ ID NO: 3           moltype = DNA   length = 21
FEATURE                Location/Qualifiers
source                 1..21
                       mol_type = other DNA
                       organism = synthetic construct
misc_feature           1..19
                       note = RNA fragment
misc_feature           20..21
                       note = DNA fragment
SEQUENCE: 3
gtggagaagt ctgccgttat t                                             21

SEQ ID NO: 4           moltype = RNA   length = 21
FEATURE                Location/Qualifiers
source                 1..21
                       mol_type = other RNA
                       organism = synthetic construct
SEQUENCE: 4
taacggcaga cttctccaca g                                             21

SEQ ID NO: 5           moltype = AA    length = 7
FEATURE                Location/Qualifiers
source                 1..7
                       mol_type = protein
                       organism = synthetic construct
SEQUENCE: 5
ALAHKYH                                                              7

SEQ ID NO: 6           moltype = AA    length = 7
FEATURE                Location/Qualifiers
source                 1..7
                       mol_type = protein
                       organism = synthetic construct
SEQUENCE: 6
GGGSSGS                                                              7

SEQ ID NO: 7           moltype = AA    length = 394
FEATURE                Location/Qualifiers
source                 1..394
                       mol_type = protein
                       organism = synthetic construct
SEQUENCE: 7
AATMVHLTPE EKSAVTALWG KVNVDEVGGE ALGRLLWYPW TQRFFESFGD LSTPDAVMGN   60
PKVKAHGKKV LGAFSDGLAH LDNLKGTFAT LSELHCDKLH VDPENFRLLG NVLVCVLAHH  120
FGKEFTPPVQ AAYQKVVAGV ANALAHKYHG GGSGSMVSKG EELFTGVVPI LVELDGDVNG  180
HKFSVSGEGE GDATYGKLTL KFICTTGKLP VPWPTLVTTF TYGVQCFARY PDHMKQHDFF  240
KSAMPEGYVQ ERTIFFKDDG NYKTRAEVKF EGDTLVNRIE LKGIDFKEDG NILGHKLEYN  300
YNSHKVYITA DKQKNGIKVN FKTRHNIEDG SVQLADHYQQ NTPIGDGPVL LPDNHYLSTQ  360
SALSKDPNEK RDHMVLLEFV TAAGITLGMD ELYK                              394

SEQ ID NO: 8           moltype = AA    length = 150
FEATURE                Location/Qualifiers
source                 1..150
                       mol_type = protein
                       organism = synthetic construct
```

```
SEQUENCE: 8
AATMVHLTPE EKSAVTALWG KVNVDEVGGE ALGRLLVVYP WTQRFFESFG DLSTPDAVMG    60
NPKVKAHGKK VLGAFSDGLA HLDNLKGTFA TLSELHCDKL HVDPENFRLL GNVLVCVLAH   120
HFGKEFTPPV QAAYQKVVAG VANALAHKYH                                    150
```

cGMP EXOSOME LOADED THERAPEUTICS FOR TREATING SICKLE CELL DISEASE

CROSS-REFERENCE TO RELATED APPLICATIONS

This application is a continuation-in-part of and claims priority to (1) U.S. application Ser. No. 16/688,954, filed Nov. 19, 2019 (now abandoned), which is a continuation-in-part of U.S. application Ser. No. 16/591,502, filed Oct. 2, 2019 (now abandoned) and, Ser. No. 16/591,483, filed Oct. 2, 2019 (now abandoned), and claims priority to U.S. Provisional Application Nos. 62/769,123, filed Nov. 19, 2018; 62/769,774, filed Nov. 20, 2018; 62/769,711, filed Nov. 20, 2018; and 62/770,640, filed Nov. 21, 2018; (2) U.S. application Ser. No. 16/688,944, filed Nov. 19, 2019 (now abandoned), which is a continuation-in-part of U.S. application Ser. No. 16/591,502 (now abandoned), filed Oct. 2, 2019 and Ser. No. 16/591,483 (now abandoned), filed Oct. 2, 2019, and claims priority to U.S. Provisional Application Nos. 62/769,123, filed Nov. 19, 2018; 62/769,774, filed Nov. 20, 2018; 62/769,711, filed Nov. 20, 2018; and 62/770,640, filed Nov. 21, 2018; (3) U.S. application Ser. No. 16/591,502, filed Oct. 2, 2019 (now abandoned), which claims priority to U.S. Provisional Application Nos. 62/740,396, filed Oct. 2, 2018 and 62/769,123, filed Nov. 19, 2018; and (4) U.S. application Ser. No. 16/591,483, filed Oct. 2, 2019 (now abandoned), which claims priority to U.S. Provisional Application Nos. 62/740,396, filed Oct. 2, 2018, 62/740,382 filed Oct. 2, 2018, and 62/740,391 filed Oct. 2, 2018. The contents of each of the foregoing applications are incorporated herein by reference in their entireties.

REFERENCE TO THE ELECTRONIC SEQUENCE FILE

The contents of the electronic sequence listing (EXTH_001_13US_SeqList_ST26.xml; Size: 12,245 bytes; and Date of Creation: Oct. 31, 2024) are herein incorporated by reference in its entirety.

DESCRIPTION

Background of the Invention

The present invention generally relates to extracellular vesicles for therapeutic delivery, and more specifically to compositions and methods of producing exosomes that include therapeutics to correct mutation in the single nucleotide polymorphism (SNP) rs334 in chromosome 11, and treat sickle cell diseases in humans and in animals.

Sickle cell disease (SCD) encompasses a group of hematologic disorders caused by a single nucleotide-single gene mutation transversion from a normal adenine to thymine in one or both alleles in chromosome 11 in the SNP rs334. The transversion of an adenine (a purine) to a thymine (a pyrimidine) in a DNA sequence causes the transcription of an abnormal hemoglobin (also called 'S' hemoglobin 'Hb') that causes intermittent or permanent episodes of ischemia and/or infarction. Sickle hemoglobin changes the anatomy and elastic properties of normal hemoglobin and make red blood cells contained in sickled hemoglobin more viscous with less capacity to transport and deliver oxygen and nutrients to distal organs and tissues. Sickle cells have a 'C' shape with earlier cell mortality in comparison with normal red blood cells. Sickle cells accumulate easily in small vessels causing or precipitating coagulation or thrombosis resulting in vessel occlusions or sub-occlusions precipitating pain attacks, strokes, infarctions, etc. This highly impacts the life expectancy and quality of life of SCD patients. In severe forms of SCD, both alleles are affected with a translocation of thymine (T) instead of adenine (A) in SNP rs334. Homozygous sickled hemoglobin, the most severe form, is commonly known as sickle cell anemia in which both alleles are affected (T/T). Heterozygous sickled hemoglobin, a milder form of SCD, affects only one allele (A/T) and patients may or may not manifest signs or symptoms including significant pain and disability due to strokes and infarctions.

Gene therapy has proven to be efficacious in the clinic as supported by FDA approved drugs for restituting proteins associated with specific diseases. A limitation of gene therapies using a virus include deep genome off target integration issues with the potential of inducing teratogenesis and have the potential to infect other individuals that are in contact with the patient. Specifically, voretigene neparvovec uses adeno-associated virus (AAV) 2, which poses low transduction rates and exposure safety risks due to the development of AAV antibodies. Further, the density of viral copies present in body fluids can pose infection risks to other persons in close contact with a patient. See, e.g., Feria, R. et al., *Non-clinical Safety and Efficacy of an AAV2/8 Vector Administered Intravenously for Treatment of Mucopolysaccharidosis Type VI.* Mol Ther Methods Clin Dev 6, 143-158 (2017), the contents of which are herein incorporated by reference in its entirety. The current standard in drug development for SCD involves bone marrow ablation and use of ex vivo lentiviruses. To that end, treatments include hemotransfusions, human leukocyte antigen (HLA)-compatible bone marrow transplantation, and increasing fetal hemoglobin using lentivirus and chemotherapy to ablate the native bone marrow. Bone marrow ablation has undesired effects on pediatric bone and brain development. See, e.g., Bath, L. F. et al. *Bone Turnover and Growth during and after Chemotherapy in Children with Solid Tumors.* Pediatr Res 55, 224-230 (2004); lyer, N. S. et al. *Chemotherapy-only treatment effects on long term neurocognitive functioning in childhood ALL survivors: a review and meta-analysis.* Blood 126, 346-353 (2015), the contents of which are herein incorporated by reference in its entirety. Alternatively, drugs (e.g., ticagrelor) to decrease the viscosity of the red blood cells or to inhibit platelet clogging of the arteries are being tested in clinical trials. Such therapeutics aim to target SCD symptoms rather than the SCD genetic defect. Further, current treatment approaches raise ethical, logistical, and scientific concerns about treatment viability.

Currently, researchers are testing viral vectors as a drug delivery system. A primary limitation of using viral vectors in gene therapy is that such lentiviruses are known to integrate into a host cell genome and subsequently create permanent changes in the host cell genome. The resulting effects can be irreversible, for example, in engrafted tissues in humans or chromosomal transversions. Using retrovirus or lentivirus as a vector in drug delivery has the advantages of transducing hematopoietic stem cells up to 40 percent (%) with high fidelity. This approach, however, is disadvantaged during in vivo delivery due to low titers, and viral DNA integration in host DNA of transgenes. Present drug developers face challenges in using viral vectors to deliver target genetic materials to specific cells and specific tissues due to the side effects of viral transfection. Both viral and non-viral vectors have shown modest to poor results and with the caveat of inducing immune responses. Using adeno-associated virus (AAV) as a vector in drug delivery has the advantages of efficient gene transfer 30 to 60 percent, enabling in vivo administration, relatively safe dosages. This approach is, however, limited by small transgenes (4.7 Kb), inconsistently stable transfer and expression, tissue tropism, and frequently immunogenic. Existing viral and non-viral vectors generate antibodies, anti-viruses or anti-carriers that limit the bioavailability and increase the safety profile of a potential therapeutic product. See e.g., Arrighetti et al., *Exosome-like nanovectors for drug delivery in cancer*. Curr Med Chem (2018); Khan et al., *Challenges and innovations of drug delivery in older age*. Adv Drug Delivery Rev (2018), the contents of which are herein incorporated by reference in its entirety.

Extracellular vesicles called exosomes are virus-free, bacteria-free, endogenous particles found in all body fluids and body compartments that are highly effective and efficient in cell communication. See e.g., Arrighetti et al., *Exosome-like nanovectors for drug delivery in cancer*. Curr Med Chem (2018), the contents of which are herein incorporated by reference in its entirety. In particular, exosomes exist in body fluids such as blood, urine, and biological secretions. The function of exosomes is to share information such as genetic material (e.g., DNA and RNA), proteins, particles, signals, etc. between cells in a rapid and efficient manner. This biological cell-to-cell communication allows specific cellular microenvironments to synchronize their function and their architecture in response to any stimulus. Exosomes are relatively small and flexible particles of 30-130 nanometers in diameter and composed of the similar materials of normal endogenous cell membranes. Hence, exosomes are highly effective and well-tolerated with minimal to no adverse effects, as a natural cell communication pathway for cells to share information among cells. Genetic material can be inserted into an exosome to be delivered to nearby or distant cells. Exosomes have the advantages of cell transduction up to 100% with high efficiency and fidelity, non-viral and non-immunogenic effects, enabling long transgenes, RNA, proteins, etc. Presently, exosome-mediated drug delivery is challenged by the lack of readily available current good manufacturing practices (cGMP) to produce clinical-grade exosomes, and such exosomes that are available include a very low volume of exosomes containing cargoes such as large proteins or antibodies readily available for use in treating human diseases. Further, exosomes can be used as a safe, natural carrier of diagnostics or therapeutic agents in humans. See e.g., Wei et al., *Exosomal miR-7246 in body fluids is a potential biomarker for gastrointestinal cancer*. Biomark Med 2018; Chiriaco et al., *Laban-Chip for Exosomes and Microvesicles Detection and Characterization*. Sensors (Basel) 18 (10) (2018), the contents of which are herein incorporated by reference in its entirety.

As such, during wet lab testing, numerous existing protocols were followed, but they failed to produce the positive-unexpected results as indicated herein. For example, during exosome extraction the following, existing protocol failed because crystalized exosomes formed instead of viable cGMP exosomes:

1) Centrifuge the cell culture media at 300 g at 4° C. for ten minutes to remove detached cells.
2) Collect the supernatant and centrifuge at 12,000 g at 4° C. for two hours.
3) Collect the supernatant and discard the pellet.
4) Ultracentrifuge the cell culture media at 200,000 g at 4° C. for two hours.
5) Discard the supernatant and resuspend the pellet (EV) in PBS/Saline.
6) Store the EV at −B0° C.

In addition, during exosome loading, the following, existing protocol also failed because normal hemoglobin was not expressed:

1) Quantify the total exosome protein to load with plasmid.
2) Mix the exosome with the final concentration of plasmid in PBS or Opti-MEM.
3) Freeze the exosome-plasmid mix in −80° C. for thirty minutes and thaw it for thirty minutes at room temperature.
4) For every thaw cycle, mix with a vortex for thirty seconds.
5) A total of eight cycles of freeze and eight cycles of thaw for eight hours.

In short, the failed protocols and results indicated that no cGMP exosomes were produced, only crystalized exosomes, and thus, no expression of the transgene encoding normal hemoglobin. Therefore, the successful protocols, as described herein, produced different, unexpected, and positive results when compared to the failed, existing protocols. Other protocols have failed to produce cGMP exosomes because of the use of fetal hemoglobin and lentiviruses which did not successfully translate to correct the defect in the ORF of the HBB rs334.

There exists, therefore, a need in the art for a non-viral drug delivery system to treat the SCD genetic defect rather than remedy only the SCD symptoms. There is a need to produce safe, non-toxic, clinical-grade exosome-mediated therapeutics that pose no immunogenic effects nor detrimental genomic changes. In particular, such an approach would alleviate the required use of chemotherapy or bone marrow ablation, and does not include the use of potentially teratogenic lentiviruses or retroviruses. The application fulfills these needs and provides further related advantages. Accordingly, when the cGMP exosome is extracted, purified, and loaded with a therapeutic agent from an hMSC, it produced positive human prognoses and favorable effects in diseased humans during testing.

SUMMARY OF THE INVENTION

In one embodiment, a composition for treating sickle cell disease may include a cGMP exosome having a size range between 60 and 120 nm extracted from a human mesenchymal stem cell (hMSC) and/or a human PBMC at 320,000 g. In this embodiment, the cGMP exosome may include a hemoglobin Subunit Beta (HBB) DNA plasmid carrying a gene encoding a normal beta chain of hemoglobin and a short interference RNA (siRNA) having a corrected single-nucleotide polymorphism SNP rs334 (A) that expresses a normal hemoglobin while blocking expression of a mutated sickle cell beta chain of hemoglobin. The siRNA may further include a passenger strand (sense) and a guide strand (antisense) sufficient to bind to an erythroblast, where the erythroblast includes a CFU-E cell and a Hemoglobin A protein having an alpha chain and a mutated beta chain, wherein the mutated beta chain comprises a mutated mRNA. In another aspect of these embodiments, the cGMP exosome may include between 2.5 pg/µl and 500 pg/µL of the HBB DNA plasmid and between 0.5 pg/µl and 4.0 pg/µL of an siRNA, an NP-40 and glycerol mixture, and a quantity of a Tris hydrochloride buffer, wherein a pH of the composition is between 6.9 and 7. The HBB DNA plasmid may also include a marker sequence that encodes green fluorescent protein, a cytomegalovirus (CMV) promoter, a Kozak consensus sequence, and/or an HBB Open Reading Frame (ORF) targeting the corrected single-nucleotide polymorphism SNP rs334 (A).

In another embodiment as disclosed herein, a method for treating sickle cell disease may include steps for extracting a cGMP exosome from a human mesenchymal stem cell (hMSC) or from a human peripheral blood mononuclear cell (PBMC), purifying the cGMP exosome to a size between 60 and 120 nm, and loading into the cGMP exosome a first Hemoglobin Subunit Beta (HBB) DNA plasmid carrying a gene encoding a normal beta chain of hemoglobin that couples with an alpha chain and at least one short interference RNA (siRNA) having a corrected single-nucleotide polymorphism SNP rs334 (A) expressing a normal hemoglobin while blocking expression of a mutated sickle cell beta chain of hemoglobin. The extracting step may further include the step of ultracentrifuging the cGMP exosome at 320,000 g. Additionally, the loading step may further include creating a plurality of the cGMP exosomes, such as by way of loading a second cGMP exosome with a second HBB DNA plasmid carrying a gene encoding a normal beta chain of hemoglobin that couples with an alpha chain and a second siRNA having a corrected single-nucleotide polymorphism SNP rs334 (A) expressing a normal hemoglobin while blocking expression of a mutated sickle cell beta chain of hemoglobin. Here, the loading step may also include mixing the cGMP exosome and the first HBB DNA plasmid, freezing the cGMP exosome and the first HBB DNA plasmid mixture, and thawing the cGMP exosome and the first HBB DNA plasmid mixture.

In some embodiments, at least one of the plurality of loaded cGMP exosomes, such as the aforementioned second HBB DNA plasmid, may include a marker sequence encoding a green fluorescent protein, and the step of cycling between the freezing step and the thawing step may occur at a predetermined interval. In additional alternative embodiments, the process may further include adding a mixture of NP-40 and glycerol and balancing a pH of the loaded cGMP exosome to a range between 6.9 and 7 via Tris hydrochloride.

Beneficially, exosomes are highly effective virus-free particles that are well tolerated with minimal to no adverse effects, as they constitute a natural communication pathway for the cells to share information among themselves. An advantage is that it poses no concern about human leukocyte antigen (HLA) or major histocompatibility complex (MHC) incompatibility as the present exosomes exist in nature and come from a universal donor, such as the universal donor property of Exosome Therapeutics, Inc. Additional advantages include restoring the quality of red blood cells to improve sickle cell symptoms and prevent its ischemic cardiovascular complications.

Other features and advantages will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1A illustrates a method for producing autologous exosomes from a body fluid. FIG. 1B illustrates a method for extracting and creating cGMP exosome.

FIG. 5 illustrates a table of parameters for exosome extraction and purification.

FIG. 7A illustrates an exosome meeting cGMP standards loaded with a cargo of an inducible plasmid DNA to overexpress normal hemoglobin. FIG. 7B illustrates a method for loading cGMP exosomes loaded with a therapeutic agent. FIG. 7C illustrates a cGMP grade-exosome loaded with an HBB plasmid with GFP. FIG. 7D illustrates a cGMP grade-exosome loaded with an HBB plasmid.

FIG. 20A shows HBB expression (indicated by GFP expression, see arrows in far right panel). FIG. 20B shows normal HbA expression in erythrocyte progenitors (CFU-E).

FIG. 22A-FIG. 22B show Scanning Electron Microscope images of cGMP exosomes from hMSCs.

DETAILED DESCRIPTION OF THE PREFERRED EMBODIMENTS

Figure 1A:
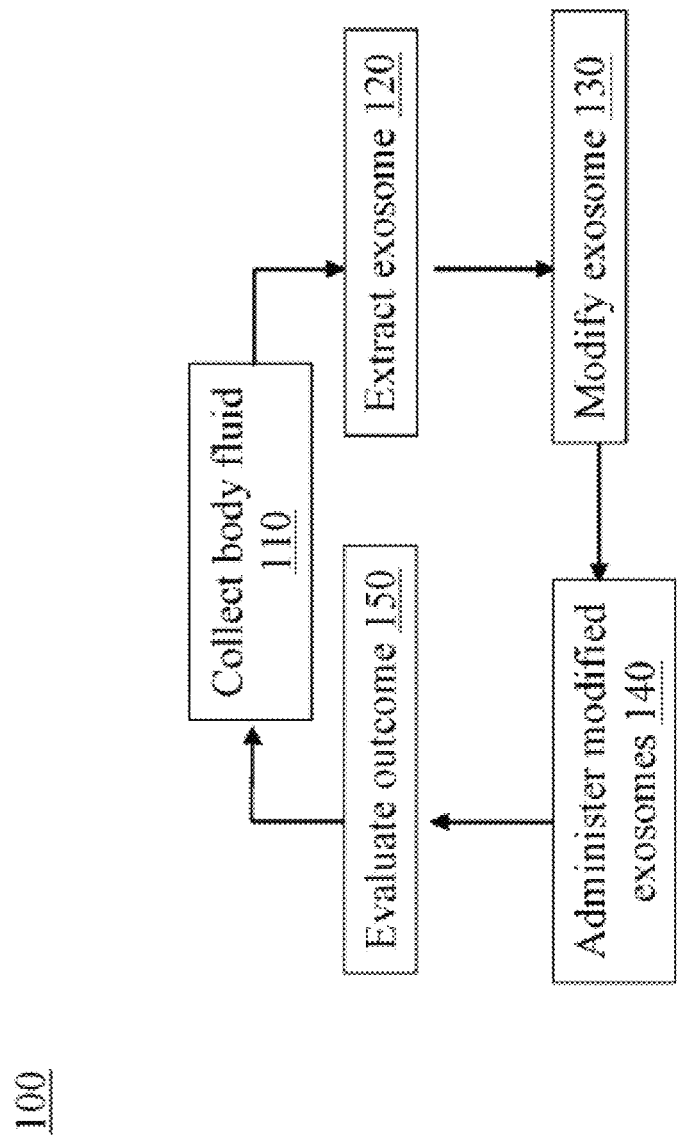
FIG. 1A-FIG. 1B illustrate a method for producing exosomes as described herein.

The term "exosome" as used herein refers to any extracellular vesicle derived from any body fluid from a human or an animal (e.g., blood), any extracellular vesicle derived from human or animal cell lines, cell cultures, and primary cultures not limited to autologous exosomes, universal donor exosomes, allogeneic exosomes, and modified exosomes. In certain examples, the exosome is made to meet pharmaceutical and cGMP.

The term "cargo" as used herein refers to any type of molecule or any type of RNA (microRNA, mRNA, tRNA, rRNA, siRNA, IRNA, regulating RNA, gRNA, long interference RNA, non-coding and coding RNA); any type of DNA (DNA fragments, DNA plasmids, iDNA); including any type of nucleic acid including antisense oligonucleotides (ASO); any genetic material; any genetic construct; any nucleic acid construct; any plasmid or vector; any protein including recombinant endogenous protein, enzyme, antibody, wnt signaling proteins; any cellular component; chimeric antigen receptor T cell (CAR-T cell) transduced without using a retrovirus; any virus including retrovirus, adenoviruses (AdV), AAV of any variety and strain, and DNA viruses; any gene editing technology including CRISPR, CRISPR/Cas9 system, any endonucleases for base editing, a Zinc finger, a single base editor, TALENs, any meganuclease; any synthetic molecular conjugate; or combination thereof loaded into an exosome. Typically, such cargo is naturally not present in the exosome and once loaded administers treatment directly to the cytoplasm of cells in tissues for treatment of diseases, including SCD. While the embodiments described herein contemplate treating sickle cell disease, the methods can be used to treat other diseases, e.g., cardiovascular disease as disclose in U.S. Publication No. 2020/0101016, the contents of which are herein incorporated by reference in its entirety; multiple oncological disorders as disclosed in U.S. Publication No. 2020/0215114, the contents of which are herein incorporated by reference in its entirety; and/or non-alcoholic steatohepatitis, diabetes mellitus type 1 and type 2, atherosclerotic cardiovascular disease, and alpha 1 antitrypsin deficiency as disclosed in U.S. Publication No. 2020/0157541, the contents of which are also herein incorporated by reference in its entirety. More specifically, the cargo can be any treatment for SCD and sickle cell anemia, including primary and secondary prevention of SCD complications, lessening pain, decreasing ischemic attacks, stroke prevention, amputation prevention, SCD pharmacotherapy, mitochondrial dysfunction, and oxidative stress. In certain examples, the cargo is made to meet pharmaceutical and cGMP standards.

In one embodiment cargo could include a promoter. The term "promoter" as used herein refers to any DNA sequence that promotes the transcription of a gene. A plasmid refers to a tissue-specific promoter. Moreover, the promoter refers to any tissue-specific promoter (e.g., lung, liver, or any other tissue type), a self-inactivating (SIN) sequence, vesicular stomatitis virus G protein (VSV-G), or a combination thereof. The advantage of using a tissue-specific promoter is to better target a desired tissue in which to transcribe RNA and subsequently encode a protein.

The term "fluid" as used herein refers to any type of body fluid produced by a human or an animal including but not limited to blood, cerebral spinal fluid, urine, saliva, and any biological secretions, etc.

As shown in the exemplary drawings for purposes of illustration, FIGS. 1-4 illustrate methods of producing exosomes and cargo and methods for exosome loading. Such improved methods and techniques would be appreciated by one of ordinary skill, especially those for increasing yield of purified exosomes and efficient loading of exosome cargo for use in preclinical and clinical studies. The methods of loading the genetic material (e.g., constructs of DNA or RNA, or any type of nucleic acids) directly into exosomes are transformation, transfection and microinjection. In one embodiment, exosomes are extracted and purified from peripheral blood mononuclear cells (PBMC) circulating in peripheral blood. In such an embodiment, PBMCs are harvested from a patient or a universal donor. PBMCs are isolated and expanded in vitro using closed systems for cell culture. In another embodiment, closed systems may be used depending on available resources. PBMCs produce and secrete exosomes into the media of a cell culture. The media can be filtered and exosomes can be sorted by specific parameters and purified to improve exosome quality.

The embodiments provide a gene therapy treatment of SCD using exosomes to deliver a genetic construct to express normal adult hemoglobin and thereby replace sickled hemoglobin with normal hemoglobin in a subject with SCD. This drug delivery can transduce human bone marrow cells to increase the pool of normal adult hemoglobin. As a result, corrected red blood cells shape and function would improve sickle cell symptoms and prevent SCD ischemic cardiovascular complications. In one instance, a composition includes an exosome loaded with a cargo of a plasmid DNA with a construct to express normal adult hemoglobin.

FIG. 1A illustrates a method for producing autologous exosomes from a body fluid according to an embodiment. Although the method 100 is illustrated and described as a sequence of steps, it is contemplated that various embodiments of the method 100 may be performed in any order or combination and need not include all of the illustrated steps. The method 100 has the step of: collecting body fluid 110 from a subject, extracting exosomes 120 from the body fluid, modifying the exosomes 130, administering modified exosomes 140, and evaluating a health-related outcome 150. A health-related outcome in the case of SCD refers to quantifying the delivery of exosomes associated with a cargo for expressing normal hemoglobin in a subject.

In step 110, body fluid is collected from a subject. The subject may be a human or an animal. The body fluid can be peripheral blood, cerebral spinal fluid, secretions, or any other body fluid in which exosomes can be extracted.

In step 120, exosomes are extracted from the body fluid. The extraction method depends on a number of factors including the type of body fluid extracted. Peripheral blood, for example, contains PBMCs and cellular component layers that can be separated by centrifugation at a medical facility. During the extraction process plasma, cells and cellular components are kept on dry ice at all times before isolation.

In one embodiment, an exosome can be modified to include a targeting agent on a surface of the exosome. Specifically, the exosomes can be modified (modified exosomes) to have specific targeting agents, such as protein epitopes and similar such targeting agents. In various examples, the modified exosomes may have a targeting agent covering an entire surface or a partial surface of the exosome. Thin layer chromatography can be used to optimally separate exosomes and exosome-related products according to specific exosome associated surface proteins and lipids. An exosome from peripheral blood, for example, would have exosome-related products such as transferrin receptors (immature exosomes), signaling molecules, and similar cellular components. In another embodiment, ionic separation by drift time can be used to optimize extracting exosomes. For example, mass spectrometry may be used to extract high yields of exosome and exosome-related products. Ion mobility spectrometry-mass spectrometry may also be performed when physicochemical properties of both the exosome and the cargo need to be defined prior to loading into the exosome. Extracted exosome samples can be purified using column methods in accordance with cGMP protocols and regulatory requirements.

In step 130, the exosomes are modified by incorporating cargoes.

In one optional embodiment, the modifications to the exosomes are done ex vivo. The exosomes can be further modified to have specific protein epitopes on its surface. Exosomes are assembled or transfected with cargo using a number of methods. In one embodiment depending on the physicochemical properties of the cargo, the exosomes are assembled or transfected with cargo using liposomes (Lipofectamine 2000, Exofect, or heat shock). In another embodiment, exosomes are assembled or transfected with cargo using CAR-T cells transduced without using retroviruses. In another embodiment, exosomes are assembled or transfected with cargo using retroviruses, AdV, AAV of any variety and strain. In another embodiment, exosomes are assembled or transfected with cargo using DNA viruses, SIRNA, long interference RNA, noncoding RNA, IRNA, RNA vectors. In another embodiment, exosomes are assembled or transfected with cargo using DNA, DNA plasmids, CRISPR, CRISPR/Cas9 and/or any endonucleases for gene editing. In another embodiment, exosomes are assembled or transfected with cargo using gene editing technology, small molecules, antibodies, and proteins including recombinant endogenous proteins. In another embodiment, exosomes are assembled or transfected with cargo using oligonucleotide therapeutics, including ASO, gene targeting technology, and gene correction technology. In another embodiment, exosomes are assembled or transfected with cargo using synthetic/molecular conjugates and physical methods for delivery of gene and cell therapeutics.

Exosomes loaded with cargo are considered mature exosomes and are inspected for cGMP compliance, purity and stability for quality assurance and quality check. Next, mature exosomes that have passed the quality check undergo an expansion process if needed. Next, the mature exosomes are diluted and premix into saline/vehicle (depending on the characteristics of the cargo) for a ready to administer tube/cartridge. Finally, the suspension is frozen and stored or shipped to a site for use in clinical or preclinical studies and to patients for self-injection of approved-clinical grade mature exosomes.

In step 140, the mature exosomes are administered to a subject. The subject, may be the same subject from which the body fluid was collected in step 110. The method of administering the exosomes 140 includes, but is not limited to: intravenous, intra-arterial, intrathecal, intra-ventricular, subcutaneous, subdermal, oral, rectal, intra-peritoneal, transdermal, intraosseous injection, intraosseous infusion, or a combination thereof. In one embodiment the mature exosomes are administered in vivo. Accordingly, once the erythrocytes containing functional hemoglobin molecules are generated in vivo, those erythrocytes have a longer lifespan in vivo than erythrocytes that were homozygous for the sickle-cell allele.

In step 150, the outcome of the treatment is evaluated. This evaluation can be done using a variety of methods, which is immediately apparent to one of ordinary skill in the art.

Figure 1B:
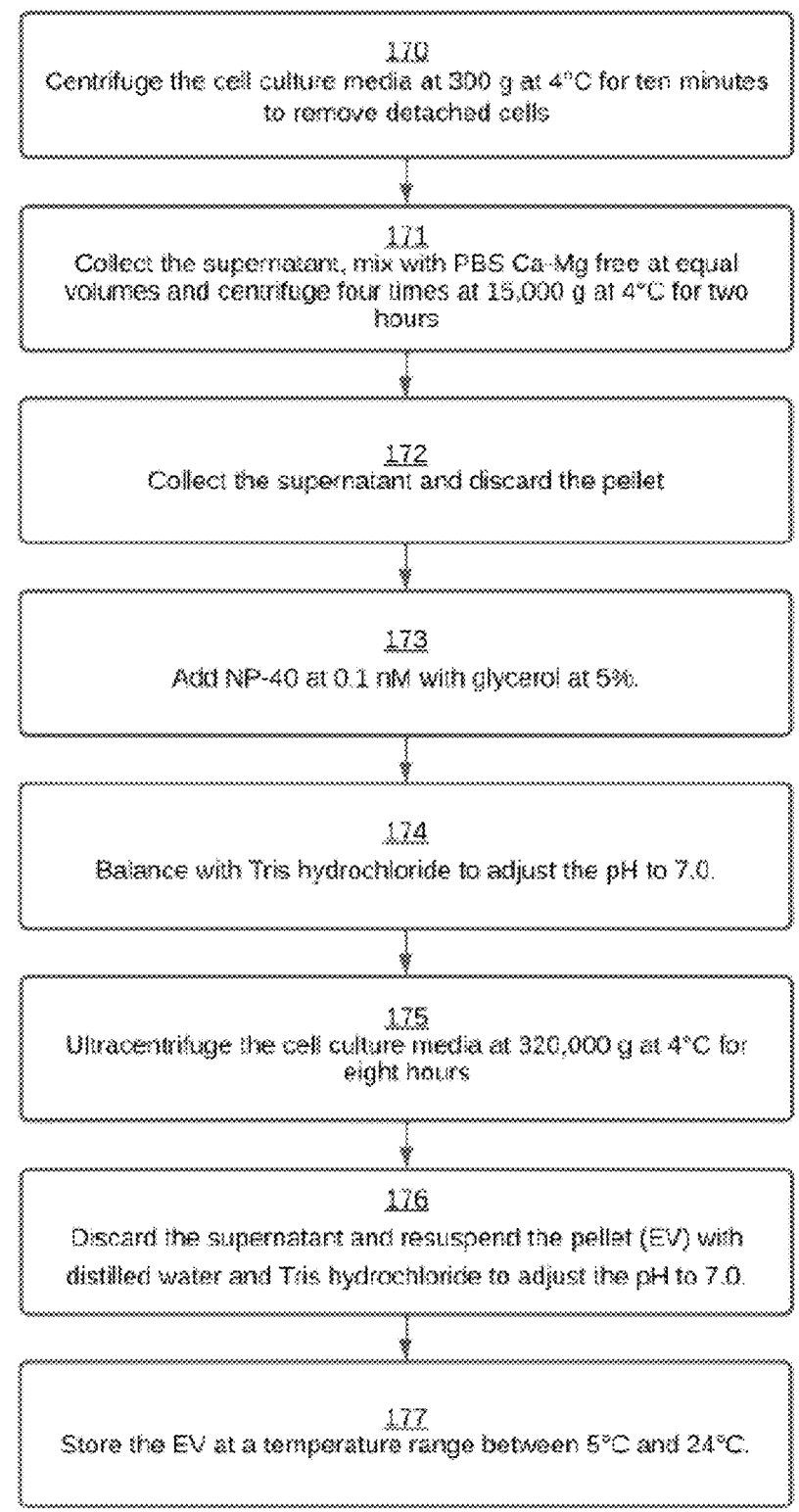

FIG. 1B demonstrates one embodiment to produce cGMP exosomes, where human mesenchymal stem cells (hMSC) are harvested from a body fluid or other media and isolated, the implementation of which would be apparent to one of ordinary skill in the art. Importantly, the hMSCs allow 100% confluency in all harvested media. The MSCs are cultured with ultracentrifuged Fetal Bovine Serum (FBS) at 200,000 g for twelve hours. Thus, no FBS-derived exosomes are used. FBS-derived exosomes affected the purity of the cGMP exosomes and interfered with the effectiveness of the therapeutic during wet lab testing. Because FBS-derived exosomes contain non-cGMP exosomes and other genetic material, they interfered with correcting for the normal expression of hemoglobin. Accordingly, FBS-derived exosomes are not implemented in any embodiment Continuing with the previous embodiment in FIG. 1B, the exosomes are extracted utilizing the following process to produce cGMP exosomes:

(170) Centrifuge the cell culture media at 300 g at 4° C. for ten minutes to remove detached cells.
(171) Collect the supernatant, mix with PBS Ca—Mg free at equal volumes and centrifuge four times at 15,000 g at 4° C. for two hours.
(172) Collect the supernatant and discard the pellet.
(173) Add NP-40 at 0.1 nM with glycerol at 5%. NP-40 is also referred to as Tergitol-type NP-40 and nonylphenoxypolyethoxylethanol and is an ethoxylated nonylphenol for non-ionic surfactants and can act as an emulsifying and demulsifying agent.
(174) Balance with Tris hydrochloride to adjust the pH to 7.0.
(175) Ultracentrifuge the cell culture media at 320,000 g at 4° C. for eight hours.
(176) Discard the supernatant and resuspend the pellet (EV) with distilled water and Tris hydrochloride to adjust the pH to 7.0.
(177) Store the EV at a temperature range between 5° C. and 24° C.

Figure 2:
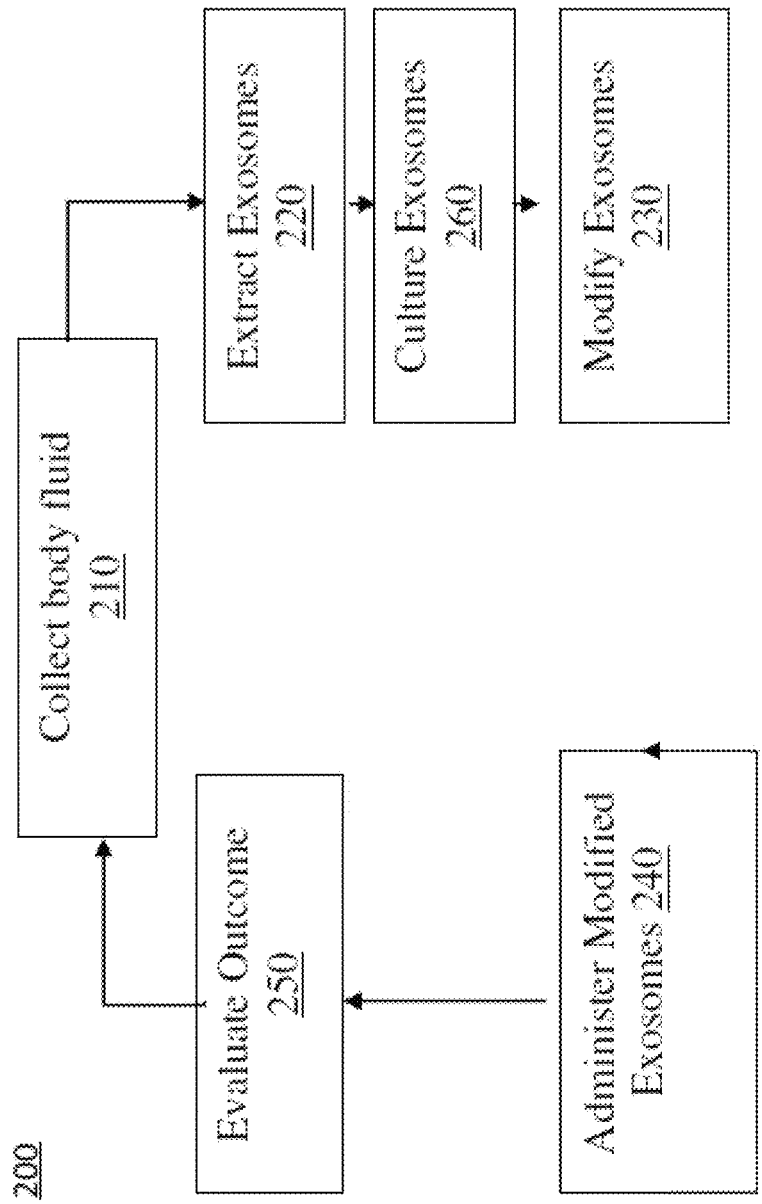
FIG. 2 illustrates a method for producing autologous exosomes, in accordance with the embodiments disclosed herein.

FIG. 2 illustrates a method for producing autologous exosomes from a body fluid according to an embodiment. Although the method 200 is illustrated and described as a sequence of steps, it is contemplated that various embodiments of the method 200 may be performed in any order or combination and need not include all of the illustrated steps. The method 200 has the step of: collecting body fluid 210 from a subject, extracting exosomes 220 from the body fluid, culture the exosomes 260, modifying the exosomes 230, administering modified exosomes 240, and evaluating the outcome 250.

In step 210, body fluid is collected from a subject. The subject may be a human or an animal. The body fluid can be peripheral blood, cerebral spinal fluid, secretions, or any other body fluid in which exosomes can be extracted. In 220, exosomes are extracted from the body fluid using methods as explained above.

In step 260 the exosomes are subjected to a primary culture and expansion. The exosomes are extracted from primary cultured cells utilizing the method in FIG. 1B. The cell culture and expansion may be frozen and stored for future exosome extraction procedures/protocols per the methods as described herein.

In step 230, the exosomes are modified by incorporating cargoes. Exosomes are purified and loaded with cargo using a number of methods as explained above. In one embodiment, the step of modifying the exosomes occurs ex vivo. Cells are isolated from a subject cell line and the exosomes are administered to the cells from the cell line. Then, the cells with the administered exosomes are reintroduced into a subject, the implementation of which would be apparent to one of ordinary skill in the art.

In step 240 the mature exosomes are administered to a subject using methods as explained above. The step of administering the modified exosomes can occur in vivo or in vitro.

In step 250, the outcome of the treatment is evaluated. This evaluation can be done using a variety of methods, which is immediately apparent to one of ordinary skill in the art.

Figure 3:
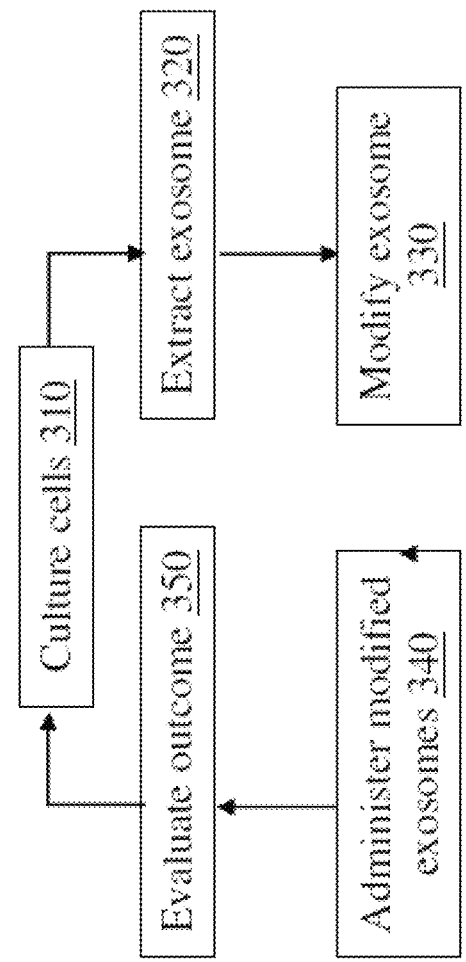
FIG. 3 illustrates a method for producing allogeneic exosomes from a cell culture.

FIG. 3 illustrates a method for producing autologous exosomes from a cell culture according to an embodiment. Although the method 300 is illustrated and described as a sequence of steps, it is contemplated that various embodiments of the method 300 may be performed in any order or combination and need not include all of the illustrated steps. The method 300 has the step of: culturing cells 310, extracting exosomes 320 from the cell culture, modifying the exosomes 330, administering modified exosomes 340, and evaluating the outcome 350.

In step 310, primary or stable cell lines of human or animal origin are cultured and expanded with standard conditions.

In step 320, exosomes are extracted from the cultured cells.

In step 330, the exosomes are modified by incorporating cargoes. Exosomes are assembled or transfected with cargo using a number of methods as explained above.

In step 340 the mature exosomes are administered to a subject using methods as explained above.

In step 350, the outcome of the treatment is evaluated. This evaluation can be done using a variety of methods, which is immediately apparent to one of ordinary skill in the art.

In one embodiment for modifying exosomes, step 330, includes purifying and transducing exosomes in vitro. In such an embodiment, the exosome undergoes in vitro testing of transduction properties such as using human bone marrow cells, and/or primary culture of PBMCs, and/or human mesenchymal stem cells, and/or the combination thereof. In an embodiment to form a cGMP exosome, an exosome undergoes transduction via a DNA plasmid construct that expresses normal hemoglobin. The loaded exosomes and therapeutic cargo are tested for stability. In such an embodiment, during step 350, the exosome compositions are delivered in vitro. Further, the loaded exosomes can be tested with human bone marrow cells and primary culture of sickle cell bone marrow and/or colony forming unit-erythroid (CFU-E) cells from patients with SCD.

Figure 4:
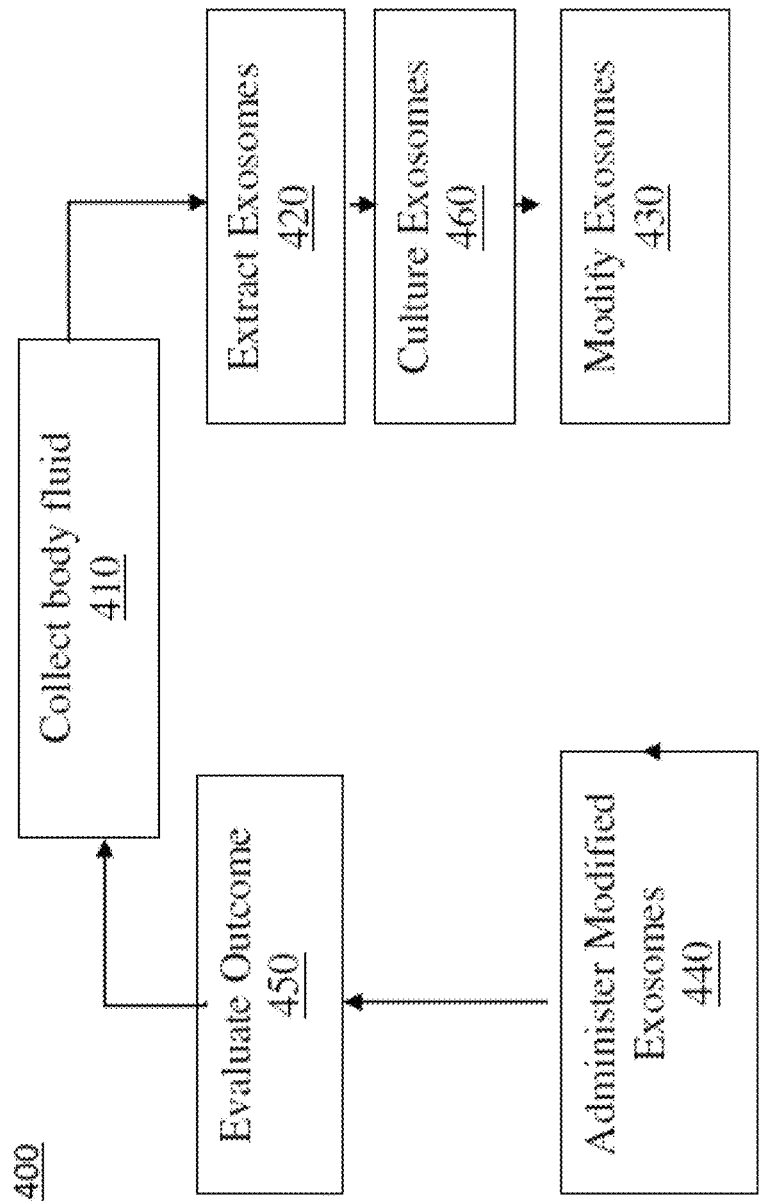
FIG. 4 illustrates a method for producing allogeneic exosomes from a body fluid.

FIG. 4 illustrates a method for producing autologous exosomes from body fluid according to an embodiment. Although the method 400 is illustrated and described as a sequence of steps, it is contemplated that various embodiments of the method 400 may be performed in any order or combination and need not include all of the illustrated steps. The method 400 has the step of: collecting body fluid 410, extracting exosomes 420 from the body fluid, culturing the exosomes 460, modifying the exosomes 430, administering modified exosomes 440, and evaluating the outcome 450.

In step 410, a body fluid is collected from a universal donor or patient. The subject may be a human or an animal. The body fluid can be peripheral blood, cerebral spinal fluid, secretions, or any other body fluid in which exosomes can be extracted.

In step 420, exosomes are extracted from the body fluid using methods as explained above.

In step 460, the exosomes are cultured. The exosomes are extracted using a primary cell culture from the body fluid of the universal donor or patient utilizing the methods taught in FIG. 1B and reproduced below:

(178) Centrifuge the cell culture media at 300 g at 4° C. for ten minutes to remove detached cells.

(179) Collect the supernatant, mix with PBS Ca—Mg free at equal volumes and centrifuge four times at 15,000 g at 4° C. for two hours.

(180) Collect the supernatant and discard the pellet.

(181) Add NP-40 at 0.1 nM with glycerol at 5%. NP-40 is also referred to as Tergitol-type NP-40 and nonylphenoxypolyethoxylethanol and is an ethoxylated nonylphenol for non-ionic surfactants and can act as an emulsifying and demulsifying agent.

(182) Balance with Tris hydrochloride to adjust the pH to 7.0.

(183) Ultracentrifuge the cell culture media at 320,000 g at 4° C. for eight hours.

(184) Discard the supernatant and resuspend the pellet (EV) with distilled water and Tris hydrochloride to adjust the pH to 7.0.

(185) Store the EV at a temperature range between 5° C. and 24° C.

The extraction protocol is highly efficient in yielding high amounts of exosomes from either body fluids or cell culture media or cell. The cell culture and expansion from the universal donor or patient may be frozen and stored for future exosome extraction procedures/protocols per the methods described herein.

In step 430, the exosomes are modified by incorporating cargoes. Exosomes are assembled or transfected with cargo using a number of methods as explained above.

In step 440 the mature exosomes are administered to a subject using methods as explained above.

In step 450, the outcome of the treatment is evaluated. This evaluation can be done using a variety of methods, which is immediately apparent to one of ordinary skill in the art.

FIG. 5 illustrates the parameters used to sort exosomes according to an embodiment. In one embodiment, autologous exosomes having a vesicle size between 60 nanometers (nM) and 120 nM are created. In certain embodiments, allogeneic exosomes have a vesicle size between about 30 nM and 130 nM. A vesicle size between 55 nM and 100 nM may be chosen as larger exosomes are less stable. Also, larger exosomes can couple with other exosomes making calculating drug dose, bioavailability, and biodistribution challenging. In some embodiments, the exosomes have the ability to expand to a size between about 60 nM and 260 nM. Such exosomes can encompass large constructs. In some embodiments, the exosomes can encompass more than or equal to about 7 kilo bases (Kb), and accommodate one or more copies of a relatively large viral particle such as an AAV. In one example, an exosome is loaded with at least four AAV particles to improve an exosome safety profile. In some embodiments, either an autologous or allogeneic exosome has a negative electrical charge. Both autologous and allogeneic exosomes can have a high membrane affinity. In some embodiments, biodistribution may be moderate to high. In a similar embodiment, potency may range from high to moderate while stability may be moderate to high.

Figure 17:
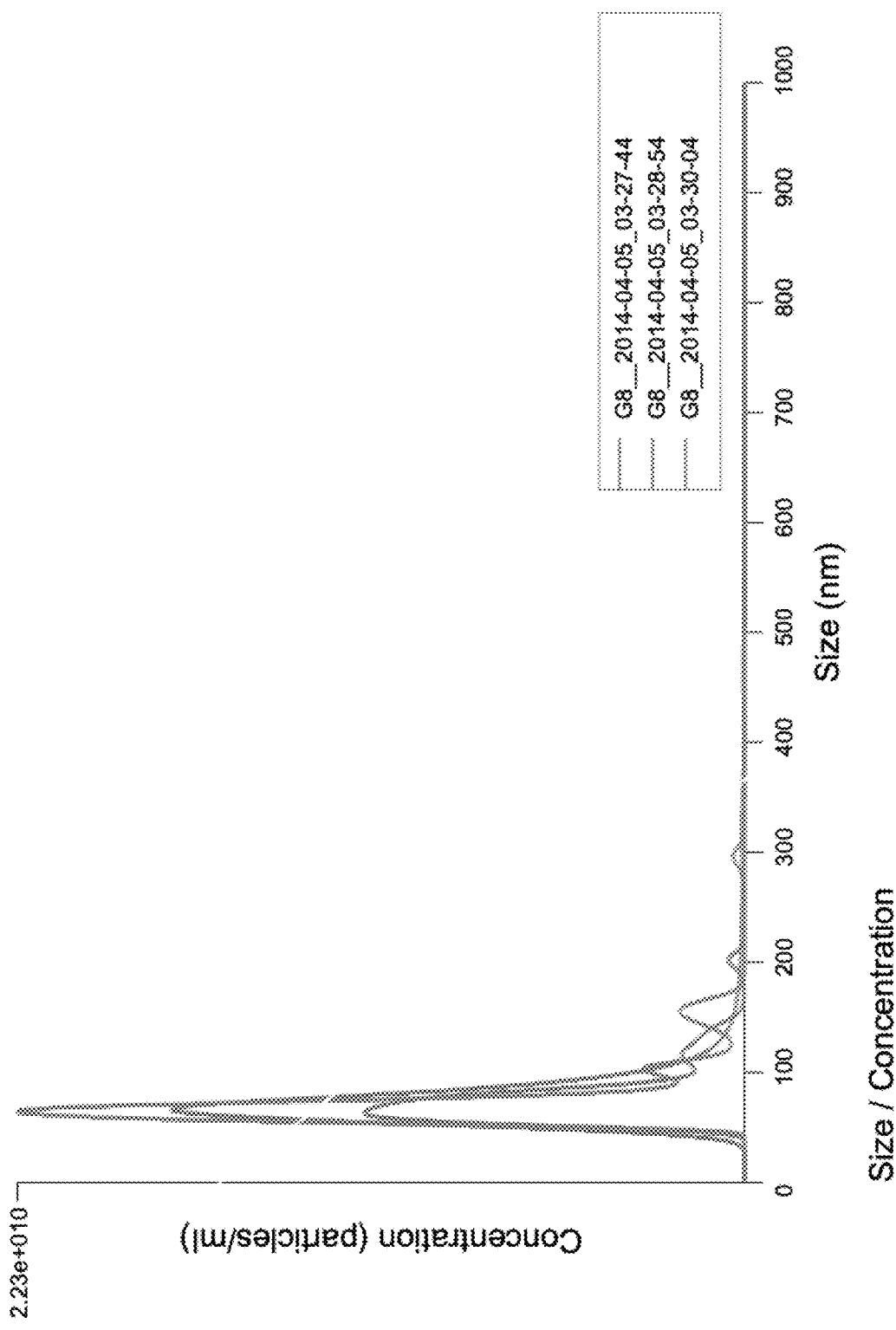
FIG. 17 illustrates purification of the exosomes described herein to a size range between 60 nM and 120 nM.

In an embodiment, the exosomes are purified to a size range between 60 nM and 120 nM, thereby creating a cGMP exosome. See FIG. 17. The cGMP exosome's size range of 60 nM-120 nM provides a spherical shape and size needed to hold a therapeutic load. For example, a plasmid with a weight of up to 2,000 kbp, large proteins, siRNA, and viruses. Advantageously, when the cGMP exosome is purified to the size range, there is zero toxicity, as shown in wet-lab testing.

In an embodiment, exosomes can have a smaller sized cargo, for example, RNA, DNA, editing tools (e.g., nucleases), or combination thereof. In another embodiment, an exosome can have a larger cargo, for example, DNA, proteins, meganucleases, or a combination thereof. One advantage of autologous exosomes is that they do not elicit a significant immune response. Allogeneic exosomes may elicit anti-drug antibodies (ADA) and neutralizing antibodies (NAb). One embodiment enables high efficiency of loading cargo into at least ninety-five percent (95%) of exosomes. Another embodiment can provide a higher purity of exosomes of at least ninety-eight percent (98%).

Additionally, an exosome can further be modified to include a targeting agent on a surface of the exosome. For example, an exosome can have specific protein epitopes, plasma membrane components, etc.

Human sickled hemoglobin arises from a mutation occurring at SNP rs334 with a transversion of thymine (T) instead of adenine (A) in one or both alleles in chromosome 11. The SCD genetic defect can be corrected by efficiently and effectively delivering exosome-mediated cargo containing genetic constructs that either deplete expression of mutated hemoglobin or express (overexpress) normal hemoglobin containing adenine at SNP rs334 (A) (also referred to herein as rs334) instead of SNP rs334 (T). Sorted and purified exosomes are loaded with a cargo for drug delivery. For clinical use in humans, the exosomes and the cargo both meet pharmaceutical or cGMP standard.

In one embodiment, during acute care of thrombotic events of SCD, the exosome-mediated cargo can be combined with low frequency ultrasound in stroke or myocardial infraction causing-thrombus to maximize the effect of thrombolytic agents (i.e., tissue plasminogen activator, etc.). Exosomes loaded with a cargo may be administered after low frequency ultrasound delivery.

Figure 6:
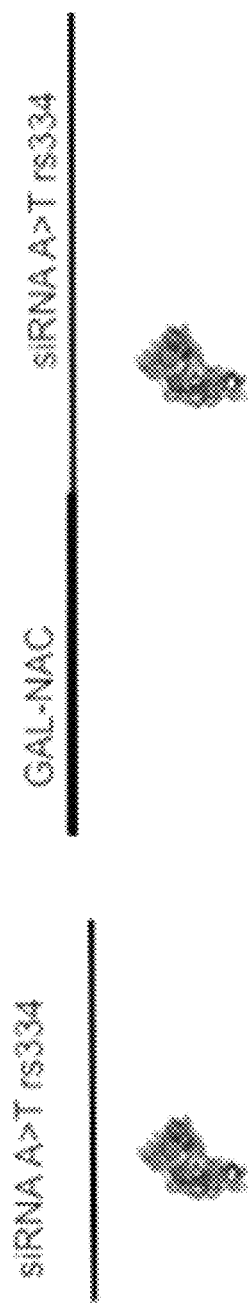
FIG. 6 illustrates a schematic of short interference RNA (siRNA) alone and siRNA used in combination with an optional N-Acetylgalactosamine (GalNAc) construct to deplete expression of mutated hemoglobin.

Gene silencing using siRNA or ASO is useful for inhibiting the translation of sickled hemoglobin and for posttranslational silencing of sickle hemoglobin in patients with SCD. FIG. 6 illustrates an optional siRNA and a siRNA-GalNAc construct used to deplete expression of mutated hemoglobin according to multiple embodiments. In this example, the siRNA has correct SNP rs334 (A) for expressing human normal hemoglobin. In one example, an exosome-mediated cargo is delivered to a subject with SCD. The cargo is loaded into an exosome for drug delivery in vivo or in vitro. In certain instances, a cargo has siRNA, a GalNAc construct, or a combination thereof to express normal hemoglobin. After the exosome-mediated cargo reaches the cytoplasm of a cell in a subject with sickle cell disease, the cargo represses the expression of sickled hemoglobin (mutated SNP rs334 (T)). In one embodiment, the siRNA and siRNA-GalNAc constructs are modified to enable greater loading efficacy and on-target mutation correction. Continuing, the cGMP exosomes carry both the gene for functional human hemoglobin beta chain alone or in combination with an siRNA silencing the translation of the mutated sickle hemoglobin.

Figure 7A:
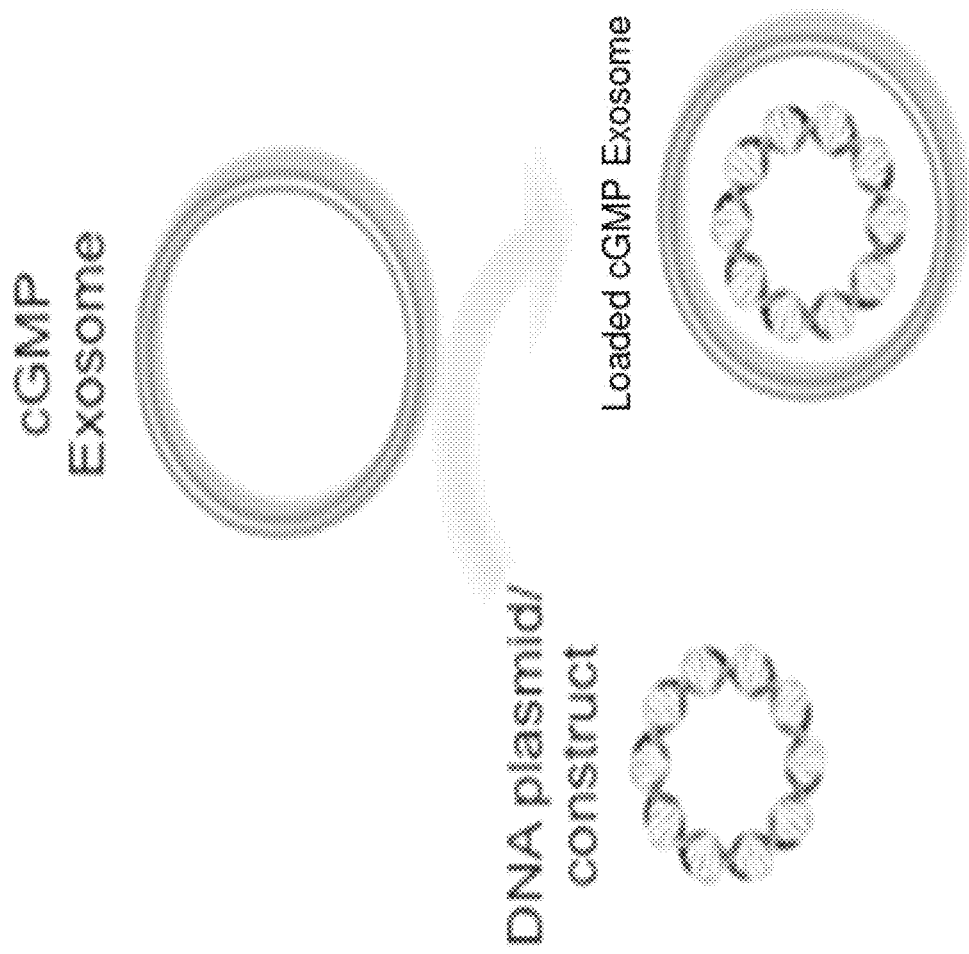
FIG. 7A-FIG. 7D illustrate loading of cGMP exosome described herein with therapeutic agents.

FIG. 7A illustrates an exosome meeting cGMP standard loaded with a plasmid DNA according to an embodiment. The embodiment provides a composition for delivering a cargo to the cytoplasm of a cell in a subject with sickle cell disease, the composition with: an exosome loaded with the cargo, wherein the cargo has a DNA plasmid and a sequence encoding normal hemoglobin, and the cargo is naturally not present in the exosome. As shown, the plasmid DNA is an inducible plasmid DNA to express or overexpress functional hemoglobin (normal hemoglobin). In this example, a cargo has a DNA plasmid and a promoter targeting a specific tissue, and a wild-type rs334 sequence expressing the correct version of rs334 (A). Optionally, the DNA plasmid includes a marker sequence encoding green fluorescent protein (GFP). In multiple examples, the DNA plasmid is induced by kanamycin, or another equivalent agent recognized by one of ordinary skill. In one example, the promoter is cytomegalovirus (CMV). In other examples, the promoter is any tissue-specific targeting promoter. The functional hemoglobin sequence encodes adult human hemoglobin. In specific examples, a cargo has siRNA, siRNA-GalNAc construct, plasmid DNA, another iRNA technology, or a combination thereof. In certain instances, a cargo includes only a DNA plasmid as a monotherapy in preclinical and clinical trials as well for human use.

Figure 7B:
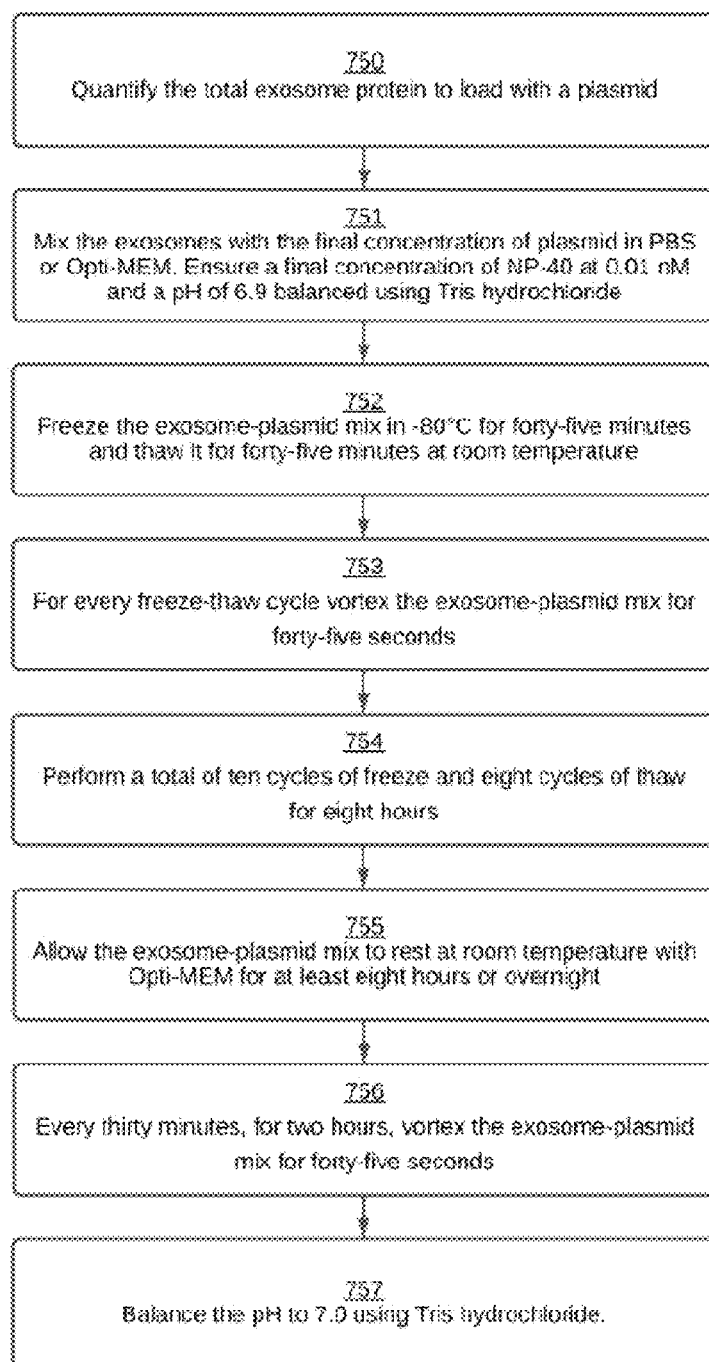

As illustrated in FIG. 7B, in one embodiment, to load cGMP exosomes with a therapeutic agent the following process was used:
  (750) Quantify the total exosome protein to load with a plasmid.
  (751) Mix the exosomes with the final concentration of plasmid in PBS or Opti-MEM. Ensure a final concentration of NP-40 at 0.01 nM and a pH of 6.9 balanced using Tris hydrochloride.
  (752) Freeze the exosome-plasmid mix in −80° C. for forty-five minutes and thaw it for forty-five minutes at room temperature.
  (753) For every freeze-thaw cycle vortex the exosome-plasmid mix for forty-five seconds.
  (754) Perform a total of ten cycles of freeze and eight cycles of thaw for eight hours.
  (755) Allow the exosome-plasmid mix to rest at room temperature with Opti-MEM for at least eight hours or overnight.
  (756) Every thirty minutes, for two hours, vortex the exosome-plasmid mix for forty-five seconds.
  (757) Balance the pH to 7.0 using Tris hydrochloride.

Figure 7C:
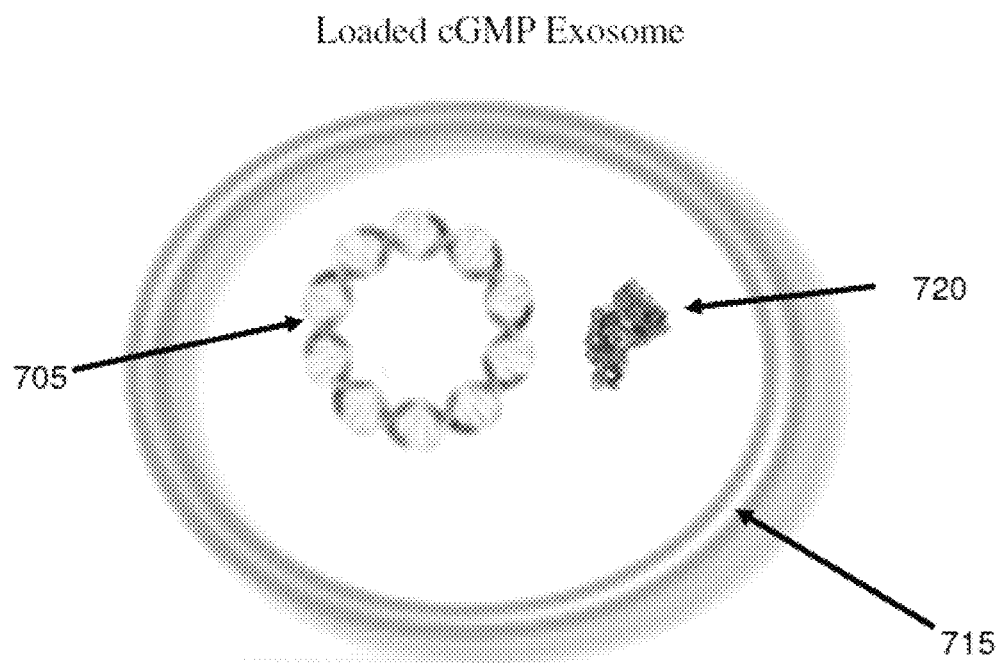

As shown in FIG. 7C, the cGMP exosome 715 acts as a carrier to transport the cargo, that includes siRNA 720 and the HBB DNA plasmid 705 carrying a gene encoding a normal beta chain of hemoglobin. The cGMP exosome 715 effectively functions as a drug delivery system (DDS) after they are extracted and purified utilizing the above methods. The HBB DNA plasmid 705, once loaded into the cGMP exosome 715 and administered to cells of a patient, the HBB DNA plasmid 705 carrying a gene encoding a normal beta chain of hemoglobin will by itself produce the normal adult beta chain without the mutation because it is carrying a gene encoding a normal beta chain of hemoglobin. The CFU-E cell will use the normal beta chain to assemble the normal adult hemoglobin. In effect, some mutated HbS will be produced by the host cell, but the ratio of normal adult hemoglobin is greater than the mutated beta chain as the non-mutated beta chain pool is greater than the mutated chain pool at the time of assembly inside of the host cell. As lab results indicate, 100% of the host cells produce the normal hemoglobin in vitro, but only 20% of cells producing normal hemoglobin will prevent sickle cell symptoms and improve quality of life and increase life expectancy. In effect, when the siRNA 720 and HBB DNA plasmid 705 are loaded into the cGMP exosome 715, a dual effect happens, where the production of normal adult hemoglobin by the HBB DNA plasmid occurs and the reduction of the host mutated sickle hemoglobin by the siRNA post translationally occurs. In one embodiment contemplated herein, the HBB DNA plasmid 705/710 carrying a gene encoding a normal beta chain of hemoglobin is loaded into the cGMP exosome 715/730 without the use of any siRNA 720/725 to produce the same beneficial outcomes. In the aforementioned embodiment of the HBB DNA plasmid 705/710 being loaded-solely-into the cGMP exosome 715, the HBB DNA plasmid 705/710 encodes for GFP and in another embodiment, does not encode for GFP. In another embodiment, the cGMP exosome 715/730 is loaded only with the siRNA 720/725, again producing the positive results described herein.

Continuing in one embodiment, as illustrated in FIG. 7C, at least a first human hemoglobin subunit beta (HBB) DNA plasmid carrying a gene encoding normal hemoglobin and with a marker sequence that encodes for green fluorescent protein (GFP) and carrying a gene encoding a normal beta chain of hemoglobin 705 is loaded into an extracted cGMP exosome 715 for treatment. Additionally loaded into the cGMP exosome 715 is an siRNA design 720 according to the below passenger strand (sense) and guide strand (antisense) sequences, where the guide strand (antisense) is sufficient silence the mutated beta chain in the erythroblast.

| Sense | Antisense |
|---|---|
| GUGGAGAAGUCUGCCGUUAUU (SEQ ID NO: 3) | UAACGGCAGACUUCUCCACAG (SEQ ID NO: 4) | and a guide strand (anti-sense) sufficient to silence the mutated beta chain in the erythroblast, which includes the Hemoglobin A protein having an alpha chain and a mutated beta chain. The mutated beta chain has mutated mRNA, which is cleaved by the siRNA at the ribosomal level. Meanwhile, the HBB DNA plasmid 705 carries the gene encoding a normal beta chain of hemoglobin. Accordingly, the non-mutated beta chain is expressed and binds to the alpha chain of the Hemoglobin A protein and forms a normal tetramer of the Hemoglobin A protein.

The first HBB plasmid 705 carrying a gene encoding a normal beta chain of hemoglobin is created via a cloning vector with a cytomegalovirus (CMV) promoter, T7 RNA polymerase, Kozak consensus sequence, a portion of the HBB Open Reading Frame (ORF), linker-emGFP, and Kanamycin to create a final HBB plasmid 705 with the CMV promoter, Kozak consensus sequence, the HBB ORF, and linker-emGFP. Concurrently filed herewith and as provided below is the corresponding HBB ORF nucleotide sequence associated with the HBB plasmid 705 and amino acid sequence. The sequence below (SEQ ID NO:7) contains a portion of one of the four frames of the HBB gene modeled to represent and express the HBB because the whole gene is too long and has too many introns and exons that cannot be included in the HBB DNA plasmid 705. For example, the AAT and ALAHKYH (SEQ ID NO: 5) portions are tailored sequences that stabilize the protein. The GGGSSGS (SEQ ID NO: 6) is a linker to bind the em-GFP with the HBB ORF.

| HBB ORF - GFP DNA Sequence | SEQ ID NO: |
|---|---|
| GGTACCGCCGCCACCATGGTGCACCTGACACCTGAAGAGAAGTCCGCCGTGACAGCCC TGTGGGGCAAAGTGAATGTGGATGAAGTTGGCGGCGAGGCCCTGGGTAGACTGCTG GTTGTTTACCCCTGGACACAGCGGTTCTTCGAGAGCTTCGGCGATCTGAGCACACCCG ATGCCGTGATGGGCAACCCTAAAGTGAAGGCCCACGGCAAGAAAGTGCTGGGCGCCT TTTCTGATGGACTGGCCCACCTGGACAATCTGAAGGGCACCTTTGCCACACTGAGCGA GCTGCACTGCGACAAGCTGCACGTGGACCCCGAGAACTTTAGGCTGCTGGGCAATGTG CTCGTGTGCGTGCTGGCCCATCACTTCGGCAAAGAATTCACCCCTCCTGTGCAGGCCGC CTACCAGAAAGTTGTTGCCGGCGTGGCAAATGCCCTGGCTCACAAGTATCATGGCGGC GGATCTGGCAGCATGGTGTCCAAAGGCGAGGAACTGTTTACCGGCGTGGTGCCCATTC TGGTGGAACTGGACGGGGATGTGAACGGCCACAAGTTTAGCGTTAGCGGCGAAGGC GAAGGGGATGCCACATACGGAAAGCTGACCCTGAAGTTCATCTGCACCACCGGCAAG CTGCCTGTGCCTTGGCCTACACTGGTCACCACCTTTACCTACGGCGTGCAGTGCTTCGC CAGATATCCCGACCATATGAAGCAGCACGACTTCTTCAAGAGCGCCATGCCTGAGGGC TACGTGCAAGAGCGGACCATCTTCTTTAAGGACGACGGCAACTACAAGACCCGGGCTG AAGTGAAGTTCGAGGGCGACACCCTGGTCAACCGGATCGAGCTGAAGGGAATCGACT TCAAAGAGGACGGCAACATCCTGGGCCACAAGCTCGAGTACAACTACAACAGCCACAA GGTGTACATCACCGCCGACAAGCAGAAAAACGGCATCAAAGTGAACTTCAAGACGCG GCACAACATCGAGGACGGCTCTGTGCAGCTGGCCGACCACTATCAGCAGAACACACCC ATCGGAGATGGCCCCGTTCTGCTGCCCGATAACCACTACCTG- - | 1 |

| HBB - GFP sequence | SEQ ID NO: |
|---|---|
| AATMVHLTPEEKSAVTALWGKVNVDEVGGEALGRLLVWYPWTQRFFESFGDLSTPDAVM GNPKVKAHGKKVLGAFSDGLAHLDNLKGTFATLSELHCDKLHVDPENFRLLGNVLVCVLA HHFGKEFTPPVQAAYQKVVAGVANALAHKYHGGGSGSMVSKGEELFTGVVPILVELDGD VNGHKFSVSGEGEGDATYGKLTLKFICTTGKLPVPWPTLVTTFTYGVQCFARYPDHMKQH DFFKSAMPEGYVQERTIFFKDDGNYKTRAEVKFEGDTLVNRIELKGIDFKEDGNILGHKLEY NYNSHKVYITADKQKNGIKVNFKTRHNIEDGSVQLADHYQQNTPIGDGPVLLPDNHYLST QSALSKDPNEKRDHMVLLEFVTAAGITLGMDELYK | 7 |

The siRNA 720 silences the translation of the mutated sickle hemoglobin by silencing the SNP rs334 mRNA. Therefore, the siRNA 720 blocks the expression of the mutated sickle cell beta chain of the hemoglobin. More specifically, the siRNA includes the passenger strand (sense)

Figure 7D:
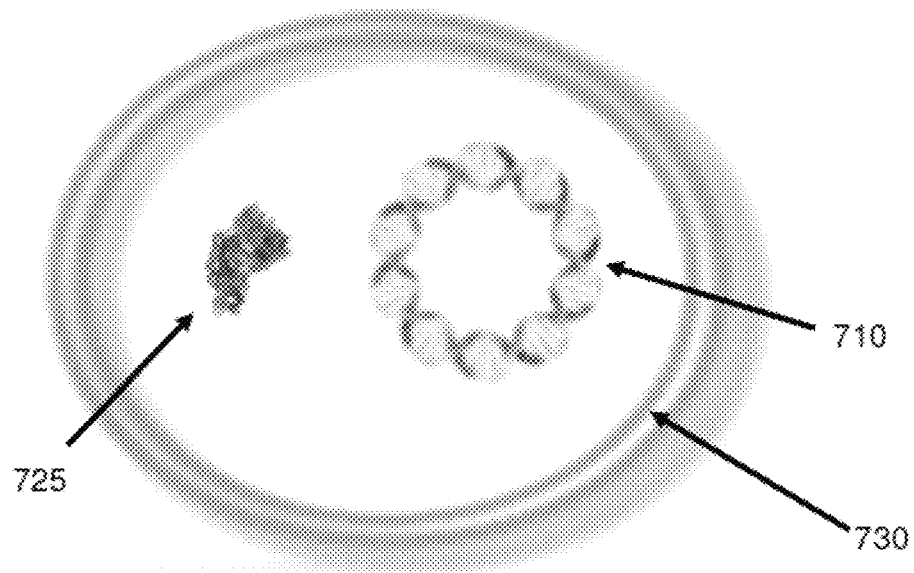

FIG. 7D illustrates at least a second HBB DNA plasmid 710 carrying a gene encoding normal hemoglobin and loaded into an extracted cGMP exosome 730 for treatment. Additionally loaded into the cGMP exosome 730 is an siRNA design 725 according to the above passenger strand (sense) and the guide strand (antisense) sequences, where the guide strand (antisense) is sufficient to silence the mutated beta chain in the erythroblast by silencing the SNP rs334 mRNA.

The second HBB plasmid 710 is created via a cloning vector that has a CMV promoter, T7 RNA polymerase, Kozak consensus sequence, the relevant HBB ORF, and Kanamycin to create a final HBB plasmid 710 with the CMV promoter, Kozak consensus sequence, and the HBB ORF. Concurrently filed herewith and as provided below is the corresponding HBB ORF nucleotide sequence associated with HBB plasmid 710 and amino acid sequence.

| HBB ORF Nucleic acid sequence | SEQ ID NO: |
|---|---|
| GCGGCGACCATGGTGCATCTGACCCCGGAAGAAAAAAGCGCGGTGACCGCGCTGTGG GGCAAAGTGAACGTGGATGAAGTGGGCGGCGAAGCGCTGGGCCGCCTGCTGGTGGT GTATCCGTGGACCCAGCGCTTTTTTGAAAGCTTTGGCGATCTGAGCACCCCGGATGCG GTGATGGGCAACCCGAAAGTGAAAGCGCATGGCAAAAAAGTGCTGGGCGCGTTTAGC GATGGCCTGGCGCATCTGGATAACCTGAAAGGCACCTTTGCGACCCTGAGCGAACTGC ATTGCGATAAACTGCATGTGGATCCGGAAAACTTTCGCCTGCTGGGCAACGTGCTGGT GTGCGTGCTGGCGCATCATTTTGGCAAAGAATTTACCCCGCCGGTGCAGGCGGCGTAT CAGAAAGTGGTGGCGGGCGTGGCGAACGCGCTGGCGCATAAATATCATTACCTGTAA TAG -- | 2 |

| HBB protein fragment | SEQ ID NO: |
|---|---|
| AATMVHLTPEEKSAVTALWGKVNVDEVGGEALGRLLVVYPWTQRFFESFGDLSTPDAVM GNPKVKAHGKKVLGAFSDGLAHLDNLKGTFATLSELHCDKLHVDPENFRLLGNVLVCVLA HHFGKEFTPPVQAAYQKVVAGVANALAHKYH | 8 |

As a result, wet lab testing showed MSCs (0.005 μg/μL, 0.5 μg/μL) in erythroblasts from patients with SCD after seventy-two hours, which provided no toxicity and nearly 100% of the cells were expressing the targeted protein. This safety profile was superior to the positive control of lipid nanoparticles which are widely used in the clinical setting for mRNA vaccines. Explicitly, lipid nanoparticles are not used in any embodiment and produced negative wet lab testing results.

Figure 18:
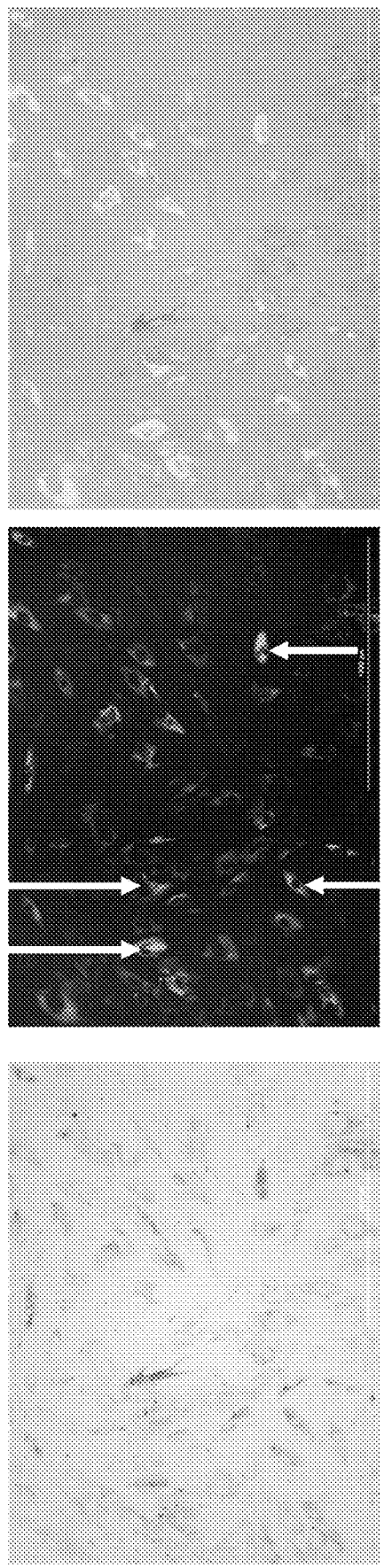
FIG. 18 illustrates HBB expression in hMSCs after treatment for 24 hours with exosomes loaded with a human HBB-GFP DNA plasmid. HBB is expression is indicated by expression of GFP (see arrows).

Evidence of wet lab testing supports that the modified HBB plasmid was effective starting at 24 hours in hMSCs to produce normal HBB, as shown in FIG. 18.

Figure 19:
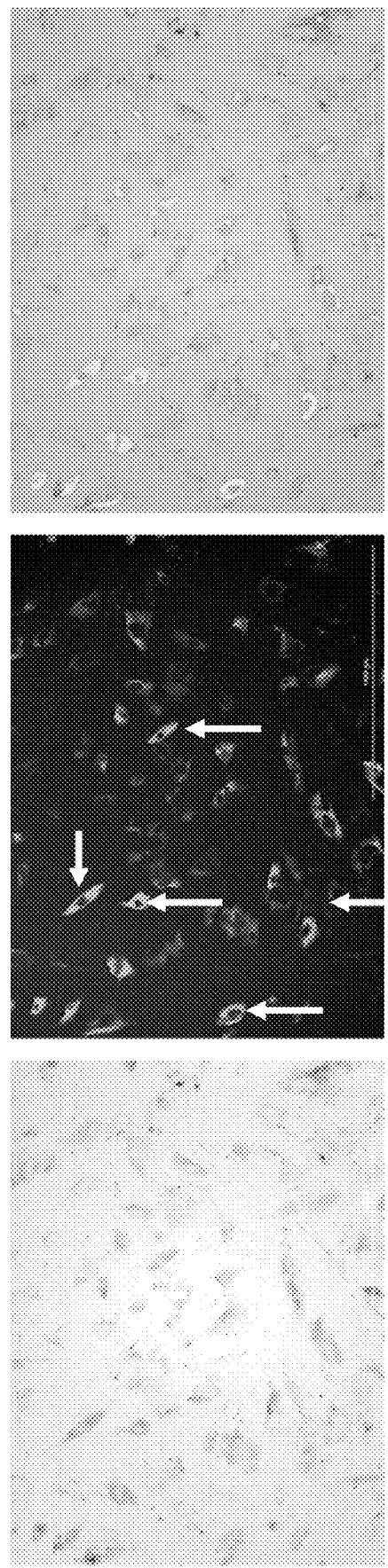
FIG. 19 illustrates HBB expression in hMSCs after treatment for 72 hours with exosomes loaded with a human HBB-GFP DNA plasmid. HBB is expression is indicated by expression of GFP (see arrows).

Continuing, evidence of wet lab testing supports that the modified HBB plasmid was effective starting at 72 hours in hMSCs to produce normal HBB and nearly 100% of the cells were expressing the targeted protein, as shown in FIG. 19.

Figure 20A:
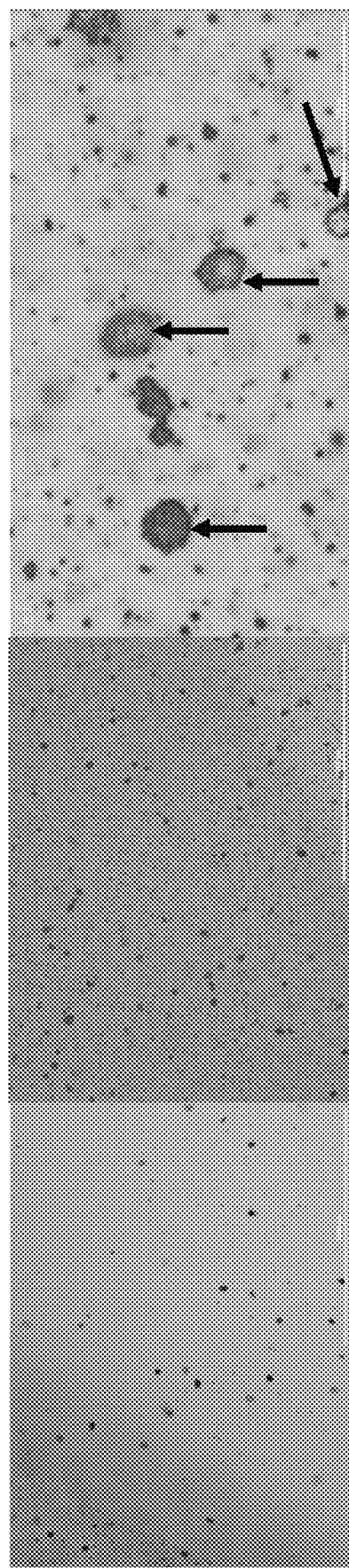
FIG. 20A-FIG. 20B illustrate HBB and HbA expression in erythrocyte progenitors after 72 hours of treatment with exosomes comprising an HBB-encoding plasmid and an siRNA targeting the rs344 SNP of the HBB gene.
Figure 20B:
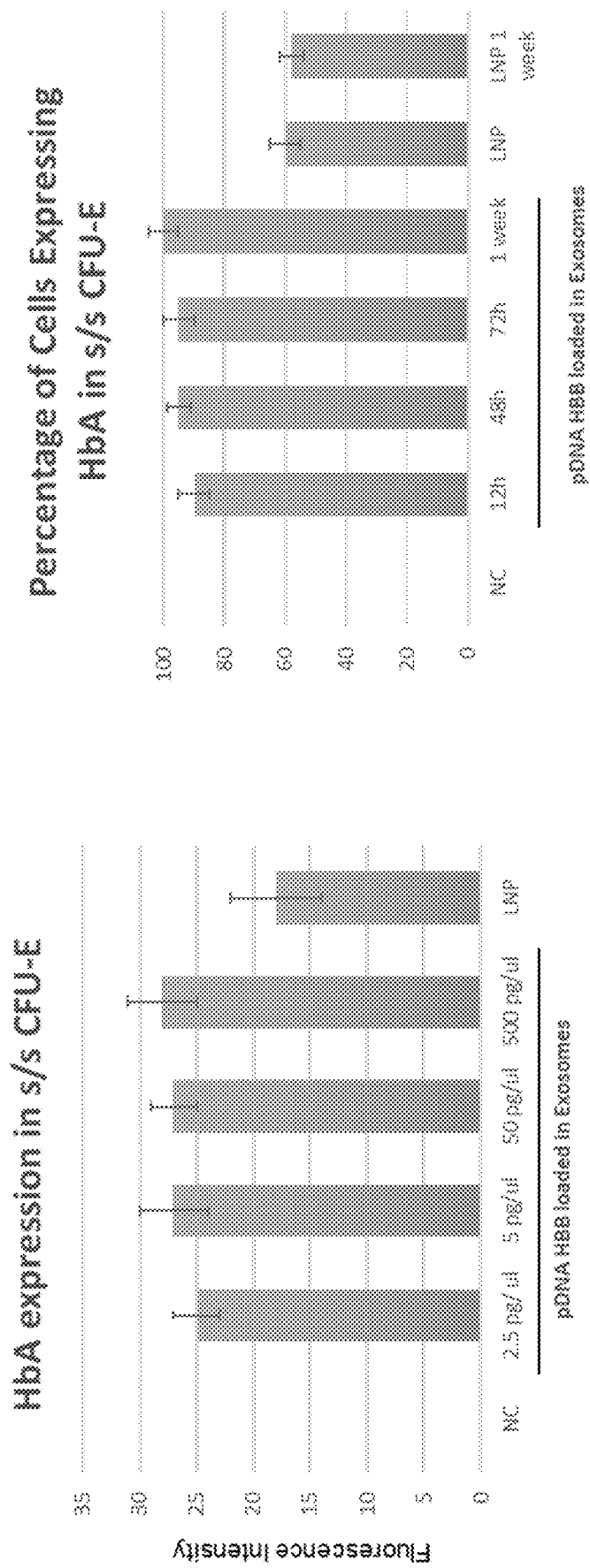

Furthermore, the wet lab results provided a high expression in 100% of cells after one week of a single treatment using the HBB plasmid loaded in cGMP exosomes at the lowest effective dose of 2.5 pg/μl in red blood progenitor cells from patients with sickle cell anemia and between 0.5 pg/μl and 4.0 pg/μL of an siRNA. Of note, the efficacy of transduction and expression was superior to the positive control of lipid nanoparticles which are widely used in the clinical setting for mRNA vaccines. These results are shown in FIGS. 20A and 20B.

Figure 21:
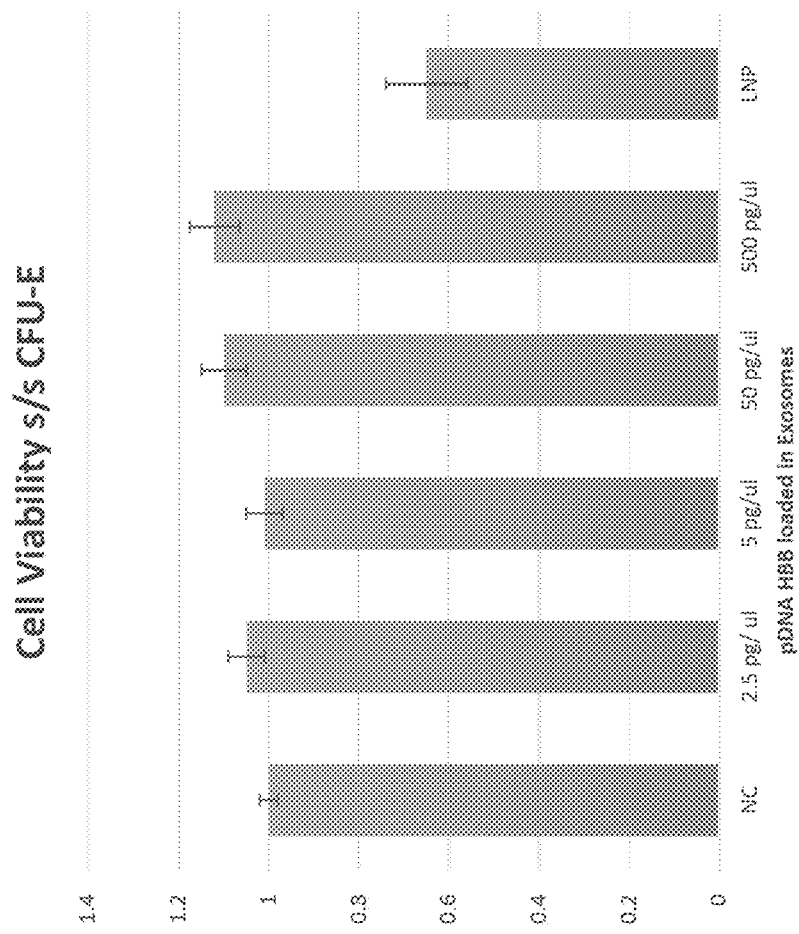
FIG. 21 shows cell viability in CFU-E cells after 72 h of treatment with pDNA-exosomes (2.5 pg/µL-0.5 µg/µL).

Moreover, the wet lab testing confirmed that there was no toxicity at increased doses of the HBB plasmid loaded into the cGMP exosomes in red blood progenitor cells from patients with sickle cell anemia. Nearly, 100% of cells were expressing the targeted protein and the safety profile was superior to the positive control of lipid nanoparticles, as shown in FIG. 21.

Additionally, more results showed successful translation of human recombinant HbA in red blood cell forming-stem cells from patients with SCD. The results indicated 95% of cells expressing the protein at 72 hours after the treatment of 2.5 pg/μL of pDNA HBB and between 0.5 pg/μl and 4.0 pg/μL of an siRNA loaded into 0.5 μg/μL of human exosomes with no toxicity. These results were superior to the positive control using lipid nanoparticles which only achieved 60% of transduction in the same patient cells and a significant cell toxicity of 40% at 72 hours. As such, the positive test results show enhanced efficacy in treating patients suffering from SCD because of the expression and transduction of normal hemoglobin with no toxicity to the targeted cells. Beneficially, the treatment is only active in erythroblasts that express the alpha subunit. HbA is conformed of subunits that include two alpha chains and two beta chains, where in sickle cell disease, the beta chain is mutated. Accordingly, the siRNA once loaded into the cGMP exosome, suppresses the expression of the corresponding mutated beta chain of the sickle hemoglobin. Meanwhile, the HBB DNA plasmid carries the gene encoding normal beta chain of hemoglobin. Therefore, a non-mutated beta chain is produced while the siRNA blocks the expression of the mutated sickle cell beta chain while allowing expression of the normal beta chain. Without the alpha chain, the protein has no function. The CFU-E cells are the only cells that have alpha subunits and conjugate into the normal tetramer of HbA.

In short, the HBB plasmid is designed to express solely the subunit beta of the normal adult hemoglobin which is mutated and dysfunctional in patients that have the homozygous mutation rs334 A>T (sickle cell anemia). Thus, the HBB plasmid will competitively couple with the alpha unit and result in normal functional adult hemoglobin in red blood cells, according to the methods described herein. Because the alpha chain is only expressed in hematopoietic cells, the plasmid has no function outside of blood derived cells, thereby producing no toxicity.

Figure 8:
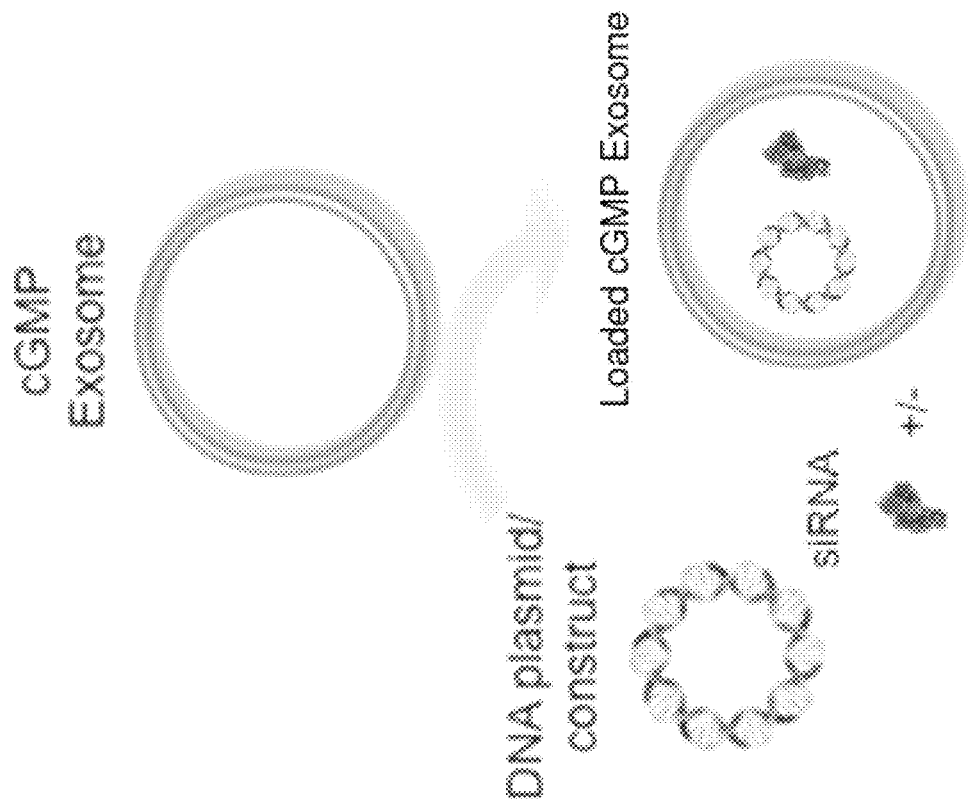
FIG. 8 illustrates a cGMP grade-exosome loaded with a cargo of an siRNA and a DNA plasmid construct.

FIG. 8 illustrates a cGMP-grade exosome loaded with cargoes of an siRNA and a DNA plasmid according to an embodiment. In an alternative example, a cGMP grade-exosome has siRNA or a DNA plasmid. A loaded exosome with a plasmid DNA construct to express normal hemoglobin and siRNA against sickle hemoglobin sequences facilitates increasing a pool of normal hemoglobin and reducing the quantity of abnormal sickle hemoglobin in vivo or in vitro. The siRNA interferes with the expression of the RS334 gene via complementary nucleotide sequences by silencing/blocking mRNA transcription of the host mutated mRNA for rs334, thereby inhibiting eventual translation of the mutated RS334 gene. Therefore, normal hemoglobin is expressed. Specifically, reducing the amount of sickled hemoglobin in erythroblasts facilitates the prospective formation of normal shaped red blood cells originating from bone marrow. The DNA plasmid expresses normal hemoglobin to restore and/or increase the pool of normal shape and function of red blood cells. Thus, sickle cell disease is treated by reestablishing hemoglobin function and improving its associated complications. The present exosome-mediated cargo significantly improves transduction efficacy and precision of delivery to cellular targets and safety profiles without immunogenicity.

Continuing, FIGS. 7-8 illustrate exosomes loaded with different types of cargo. In an embodiment, any number of cargoes discussed may be loaded into a single exosome. Further, the different types of cargo may be loaded into exosomes in any number of combinations. In one embodiment, the exosome may have one or more cargoes wherein the one or more cargoes may be identical or substantially the same. In another embodiment, an exosome may have one or more cargoes wherein each of the one or more cargoes are distinct from one another.

Figure 9:
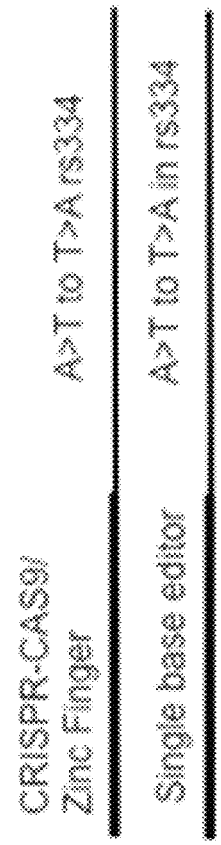
FIG. 9 illustrates a schematic of gene editing to correct thymine (T) to adenine (A) in SNP rs334 using clustered regularly interspaced short palindromic repeats (CRISPR)/Cas9, a Zinc finger, a single base editor, or a combination thereof.

In various examples, a cargo is exposed to gene editing materials to correct the SNP rs334. FIG. 9 illustrates a schematic of gene editing to correct thymine (T) to adenine (A) in the SNP rs334 using CRISPR CAS9, Zinc finger, a single base editor, or a combination thereof according to various embodiments. For example, Zinc finger domains can be engineered to target a specific desired DNA sequence and this enables a zinc-finger nuclease to target unique sequences within a genome such as SNP rs334 in SCD. By taking advantage of endogenous DNA repair machinery, these reagents can be used to precisely alter the genome by editing the SNP rs334 CRISPR-Cas9 is short for clustered regularly interspaced short palindromic repeats and CRISPR-associated protein 9. CRISPR is a highly precise gene-editing tool that relies on guide RNA (gRNA) to direct a scissor-like Cas9 enzyme to the desired spot in the genome to correct a misspelling such as thymine to adenine (A) at SNP rs334. Such CRISPR system in combination with other enzymes are used to directly install a point mutation into cellular DNA or RNA without making double-stranded DNA breaks. Typically, gene editing to modify exosomes and cargo occur ex vivo before modified exosomes having a cargo are administered to a patient. Alternatively, a cargo having a nuclease single base editor, TALENs, a meganuclease, a wnt signaling protein, or a combination thereof can be loaded into the cGMP exosome.

Figure 10:
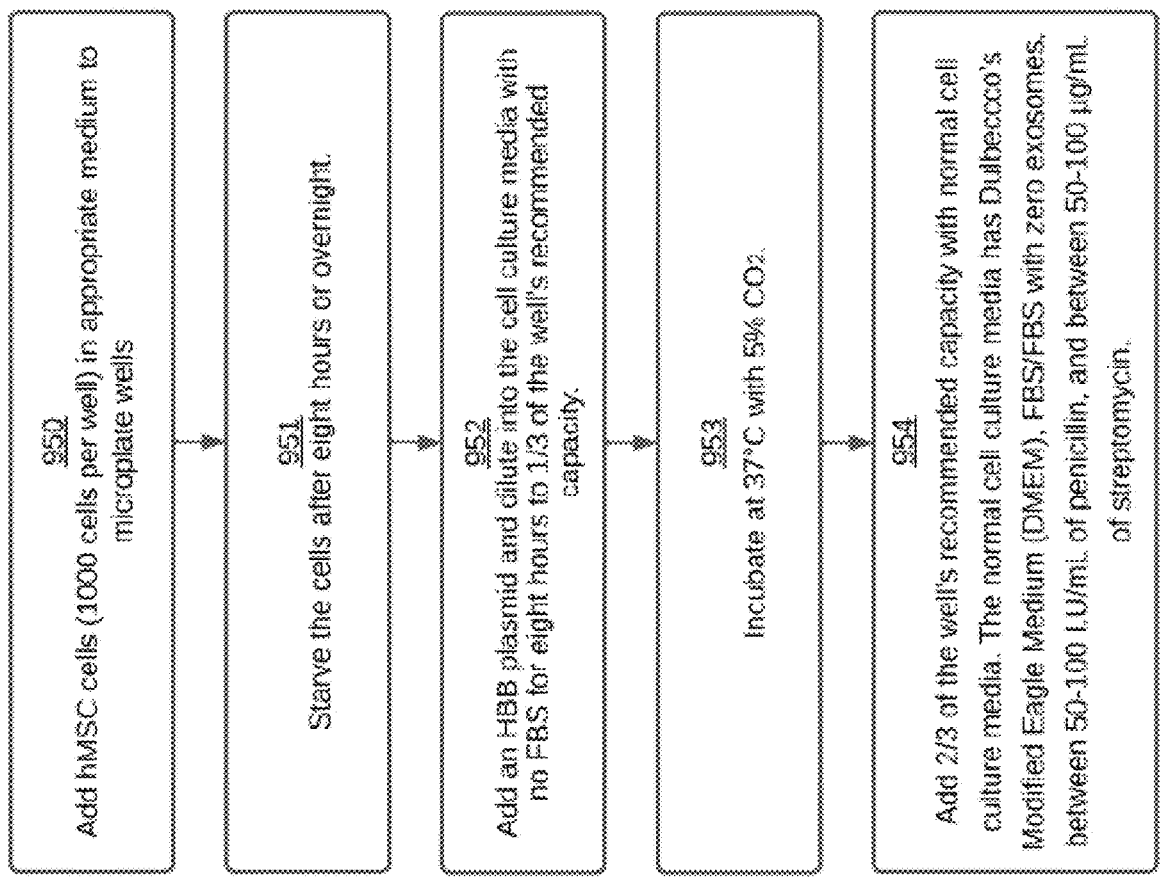
FIG. 10 illustrates a method of loading cGMP exosomes with gene editing materials to correct a SNP and produce a positive prognosis.

Additionally, as illustrated in FIG. 10, in one embodiment, after cGMP exosomes are loaded with the sequence to produce normal adult hemoglobin as described in FIG. 7B, treatment is administered utilizing the following protocol:
- (950) Add hMSC cells (1000 cells per well) in appropriate medium to microplate wells.
- (951) Starve the cells after eight hours or overnight.
- (952) Add an HBB plasmid and dilute into the cell culture media with no FBS for eight hours to ⅓ of the well's recommended capacity.
- (953) Incubate at 37° C. with 5% $CO_2$.
- (954) Add 2/3 of the well's recommended capacity with normal cell culture media. The normal cell culture media has Dulbecco's Modified Eagle Medium (DMEM), FBS/FBS with zero exosomes, between 50-100 I·U/ml of penicillin, and between 50-100 µg/ml of streptomycin.

As a result, hMSCs and human erythrocyte progenitor cells of sickle cell patients are produced. The cGMP exosomes from the hMSCs are shown in FIGS. 22A and 22B taken with a Scanning Electron Microscope Joel LB 5900 from laboratory testing.

FIG. 21 demonstrates that the cGMP exosomes were non-toxic via specified doses in wet lab testing in CFU-E cells, according the methods as described herein.

Figure 11:
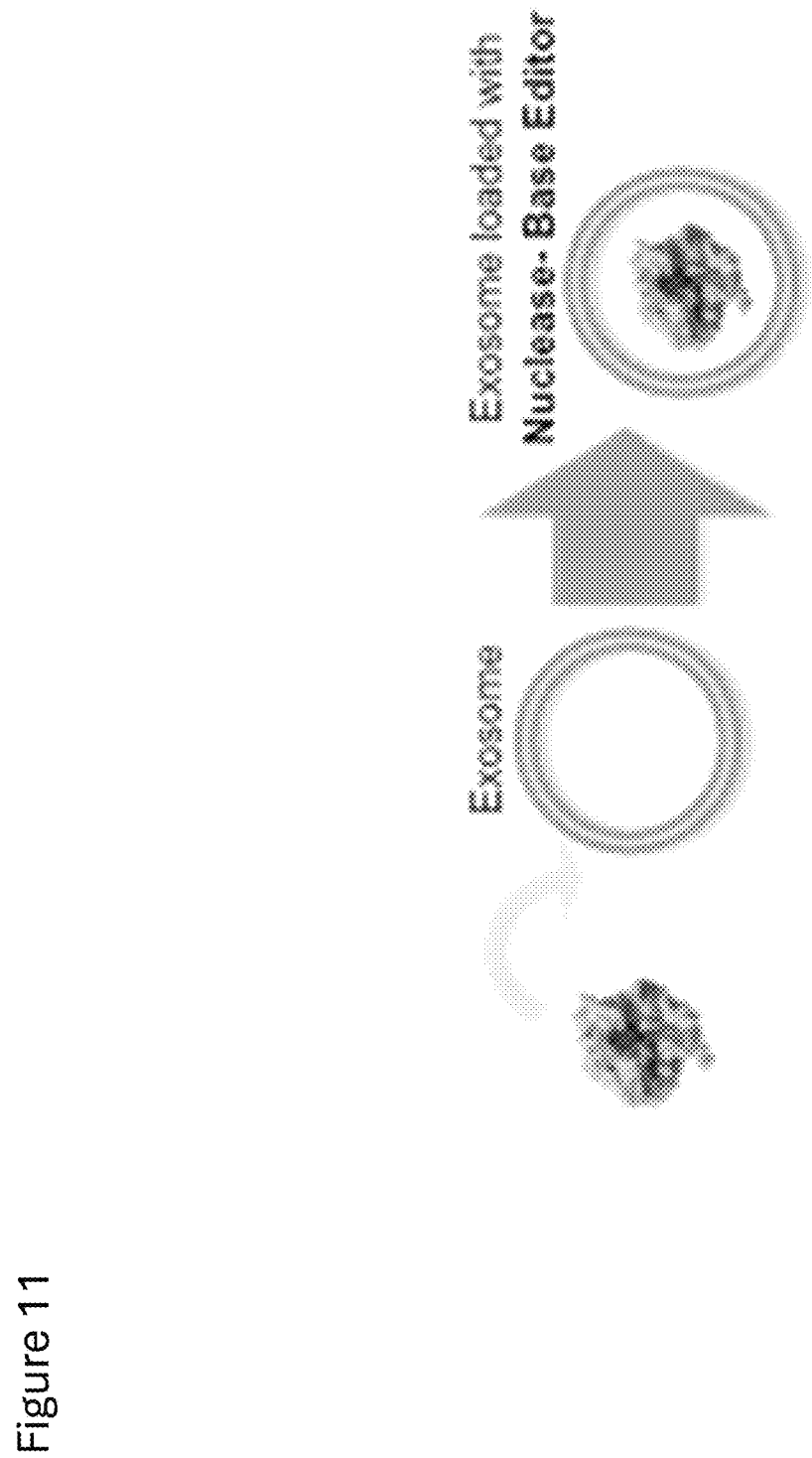
FIG. 11 illustrates a cGMP grade-exosome loaded with a cargo of a nuclease base editor.

FIG. 11 illustrates a cGMP grade-exosome loaded with a cargo of a nuclease according to an embodiment. The nuclease functions as a base editor to correct thymine for adenine in the SNP rs334. In vitro, an exosome mediated-nuclease delivery enables a nuclease to correct the base mutation in CD34+ cells carrying the SNP rs334 (T/T) or SNP rs334 (A/T). In specific examples, an exosome loaded with a nuclease base editor is delivered to the affected CD34+ cells. The base editors convert the defective sickle-cell allele or alleles to the wild-type allele or alleles (the rs334 A/A) in vitro and then the CD34+ cells are reintroduced into the patient. In an alternative embodiment, the CD34+ cells are reintroduced into the exosomes loaded with the base editor and directly injected to the bone marrow or intravenously of a patient. Base editors are the latest generation of gene editing tools with very high precision at targeting single nucleotides within a sequence. Ideally, the loaded exosomes meeting clinical-grade GMP, regulatory chemistry manufacturing and controls (CMC) compliance can be deployed to patients that suffer from SCD and its complications. The embodiment enables SCD treatment without the use of chemotherapy or bone marrow ablation using teratogenic lentiviruses or retroviruses.

One method of producing normal adult hemoglobin using CD34+ cells expressing the SCD mutation includes the step of: extracting and purifying exosomes, generating a base editor for a specific mutation or sequence, loading the base editor into an exosome, and assessing pharmacokinetics, pharmacodynamics and toxicology in vitro of the exosome-delivered base editor.

Continuing, a nuclease base editor (as described above) for SCD is designed. Base editors show very low (0.1%) indel formation (insertion or deletion of bases in the genome) which makes them safe for therapeutic use. A nuclease base editor enables treating SCD by targeting and correcting one or both alleles at SNP rs334. First, a single guide RNA (sgRNA) is designed and added to a nuclease base editor plasmid to increase precision on a target DNA sequence (SNP rs334 (T)). Second, a protospacer, protospacer adjacent motif (PAM) sequence, and motifs surrounding SNP rs334 (T) are included in the target DNA sequence. Inclusion of a protospacer and a PAM sequence enable the CRISPRCas9 system to cleave the target DNA sequence. Thirdly, the expression plasmid with sgRNA is cloned. Lastly, the sgRNA and the nuclease base editor are loaded into an exosome. A nuclease base editor corrects one or both alleles at SNP rs334.

Loading a base editor into exosomes has a proportion of loading that is 1:1 (exosome: base editor) using techniques that include electromagnetism and membrane dissociation technologies. Exosomes meeting the standards mentioned and having a vesicle size between sixty (60) and one hundred and twenty (120) nM are selected for cargo loading.

Assessing pharmacokinetics, pharmacodynamics and toxicology in vitro. In one example, an exosome loaded with a nuclease base editor is added to a media containing CD34+ cells with the SCD defect at SNP rs334 (T). Pharmacokinetic measures include: time to exosome disappearance in the media, $C_{max}$, $T_{max}$, $T_{1/2}$, etc. Pharmacodynamics include time course and dose range finding for RNA and protein detection with the corrected hemoglobin and sickle hemoglobin. Genome DNA sequencing was used to confirm the correction of the SCD mutation. Toxicology includes cell apoptosis analysis (TUNEL) and cell viability analyses (for assessing cell metabolic activity), genotoxicity (chromosome aberration, gene mutation test, DNA damage and repair, unscheduled DNA synthesis.

Figure 12:
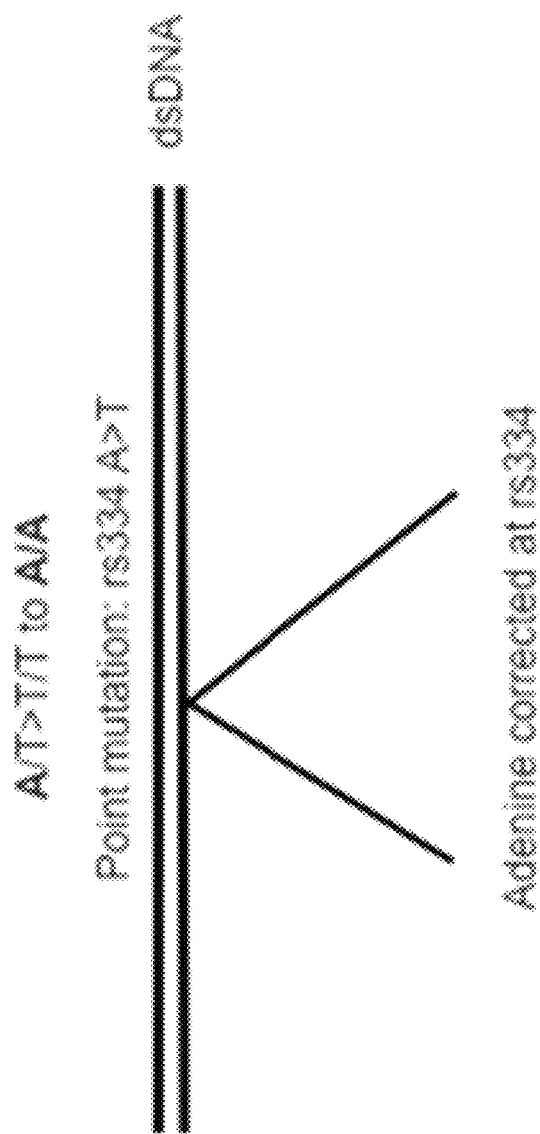
FIG. 12 illustrates insertional mutagenesis to insert a correct rs334 (A) construct into an affected allele of double-stranded DNA (dsDNA).

The SCD point mutation occurring at SNP rs334 can be corrected using insertional mutagenesis. FIG. 12 illustrates insertional mutagenesis to insert a correct rs334 (A) construct into an affected allele of double-stranded DNA (dsDNA). Transversing or exchanging the thymine (T) for adenine (A) at rs334 enables the transcription of normal hemoglobin instead of sickled hemoglobin. For example, the genotypes A/T or T/T can be corrected to A/A or A/T at SNP rs334. The constructs produced from insertional mutagenesis include plasmid DNA, transposons, and sleeping beauty transposon systems. A cargo loaded with such constructs is safe to deploy directly into animals and humans. In specific examples, the cargo loaded with such constructs undergo ex vivo engineering of a specific cell lineage such as hematopoietic stem cells (HSC), other hematic cells, any cell types in the body, cells with carrier, and cells without a carrier. The carrier is one selected from a group consisting of: an exosome, a modified exosome or a viral vector. Examples of a viral vector include a lentivirus, retrovirus, AdV and AAV which can cause permanent or transient integration into a host genome leading to short term or long term effects.

Figure 13:
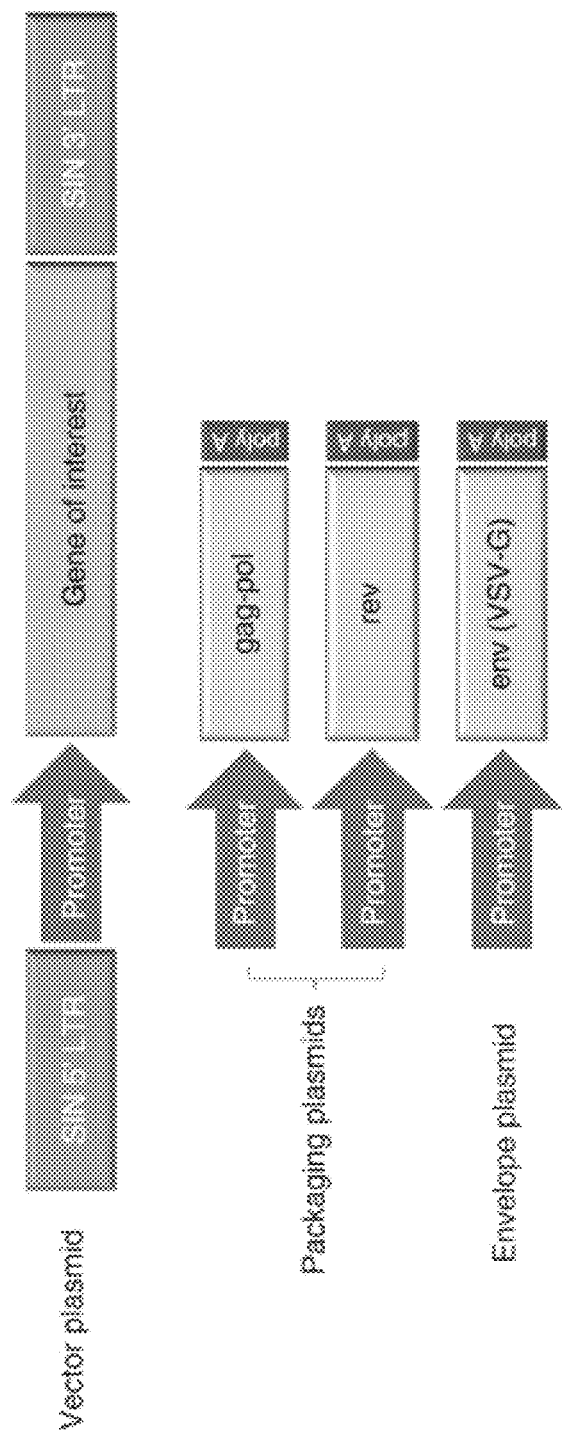
FIG. 13 illustrates a long terminal repeat (LTR), lentivirus, or retrovirus vector used to express normal hemoglobin.

Furthermore, a cargo loaded with viral vectors to express normal hemoglobin is shown in FIG. 13, which illustrates a schematic of a LTR, lentivirus/retrovirus vector used to express corrected SNP rs334. As shown, the viral vector has a tissue-specific promoter, for example, CMV. Moreover, the promoter refers to any tissue-specific promoter (e.g., lung, liver, or any other tissue type), a self-inactivating (SIN) sequence, vesicular stomatitis virus-G protein (VSV-G), or a combination thereof. The advantage of using a tissue-specific promoter is to better target a desired tissue in which to transcribe RNA and subsequently encode protein such as normal hemoglobin.

In several examples, the cGMP exosome is an autologous exosome, a universal donor exosome, or a combination thereof. In other examples, a modified exosome may have specific protein epitopes for improved efficacy of exosome loading or better exosome delivery.

Figure 14:
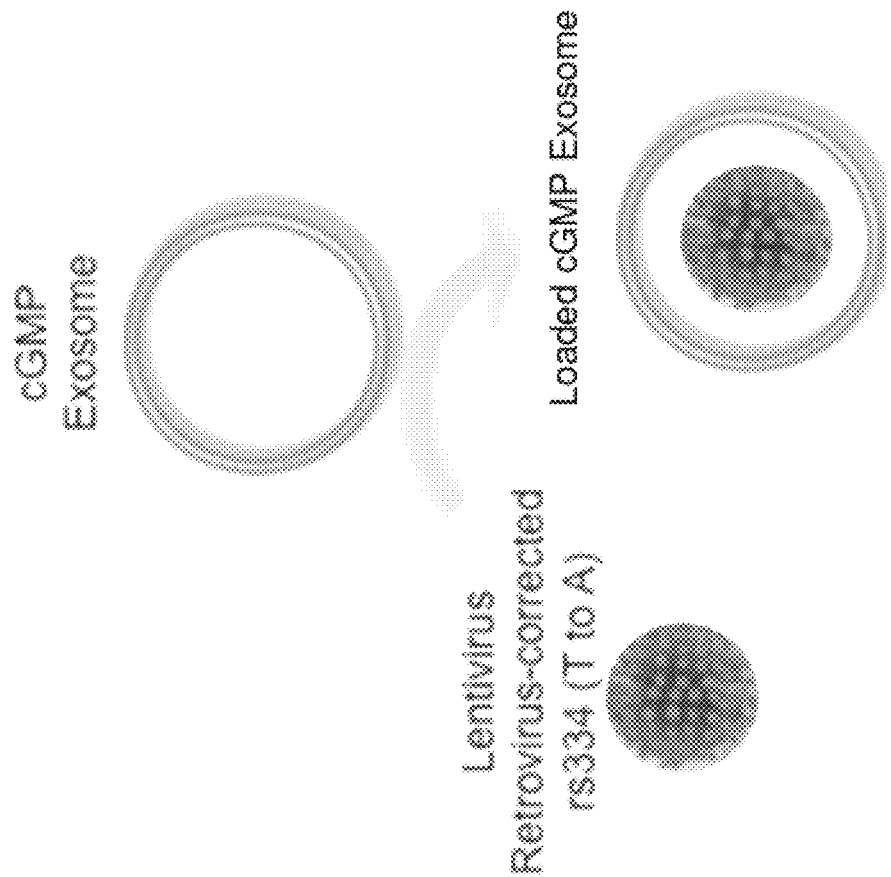
FIG. 14 illustrates a cGMP grade-exosome loaded with a cargo of a retrovirus used to express normal hemoglobin according to an embodiment.

FIG. 14 illustrates a cGMP exosome with a cargo of a retrovirus for expressing corrected rs334 according to an embodiment.

Figure 15:
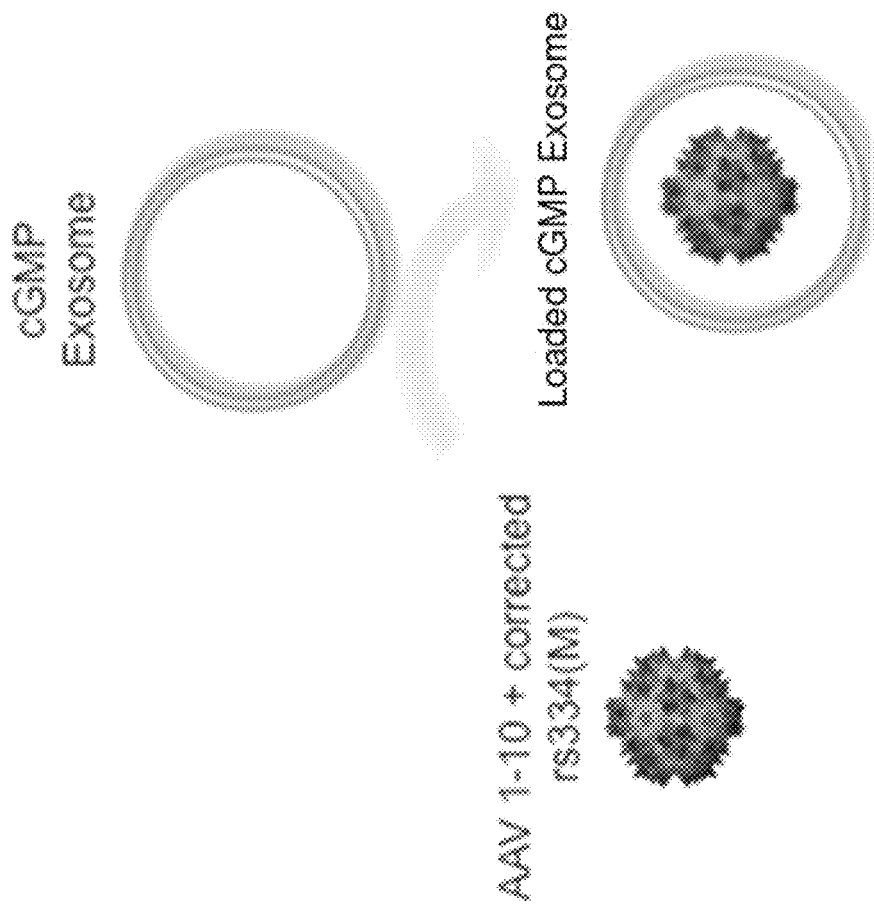
FIG. 15 illustrates loading a cGMP grade-exosome loaded with a cargo of an AAV used to express normal hemoglobin.

FIG. 15 illustrates a cGMP grade-exosome with a cargo with an AAV for expressing corrected rs334 according to an embodiment.

Figure 16:
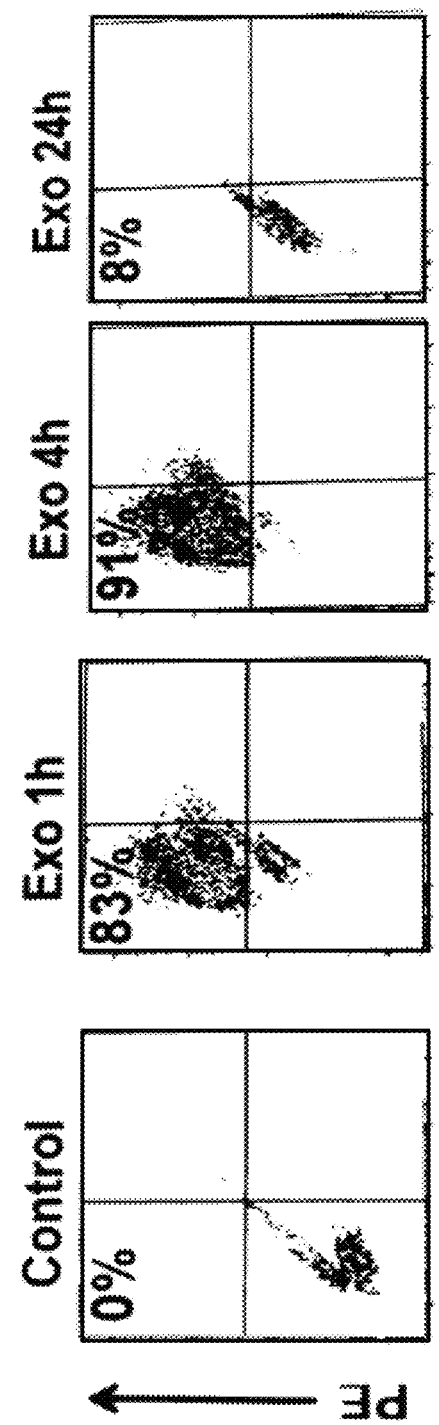
FIG. 16 illustrates a pharmacokinetic profile after in vivo administration of exosome-mediated cargo.

FIG. 16 illustrates a pharmacokinetic profile after in vivo administration of loaded exosomes according to an embodiment. The exosomes injected intravenously into an animal model of myocardial ischemia showed most exosomes were taken up by tissues in less than 24 hours. Only a smaller quantity of exosomes (8%) continued circulating after 24 hours. This data supports how the present exosomes improve in vivo delivery of cargo to tissues.

While the methods described are used to treat sickle cell disease (HbS/A, HbA/S, and HbS/S), they may be applied to treat other hemoglobinopathies, such as, but not limited to thalassemias.

Although several embodiments have been described in detail for purposes of illustration, various modifications may be made without departing from the scope and spirit of the invention. Accordingly, the invention is not to be limited, except as by the appended claims.

What is claimed is:

1. A composition comprising:
an exosome comprising:
- a DNA plasmid comprising an open reading frame (ORF) polynucleotide sequence encoding a fragment of the wild type hemoglobin Subunit Beta (HBB) protein and comprising SEQ ID NO: 2; and
- a short interference RNA (siRNA) comprising (i) a sense strand comprising SEQ ID NO: 3 and (ii) an anti-sense strand comprising SEQ ID NO: 4.

2. The composition of claim 1, wherein the exosome comprises between 2.5 pg/μL and 500 pg/μL of the DNA plasmid and between 0.5 pg/μL and 4.0 pg/μL of the siRNA.

3. The composition of claim 1, wherein the DNA plasmid further comprises a polynucleotide sequence that encodes green fluorescent protein.

4. The composition of claim 1, wherein the DNA plasmid further comprises a cytomegalovirus (CMV) promoter and a Kozak consensus sequence.

5. A method for treating sickle cell disease comprising administering the composition of claim 1 to a subject in need thereof.

6. The composition of claim 1, wherein the fragment of the wild type HBB protein consists of SEQ ID NO: 8.

* * * * *